(12) United States Patent
Matsuura

(10) Patent No.: US 7,455,976 B2
(45) Date of Patent: Nov. 25, 2008

(54) METHOD OF MEASURING OXIDIZED LDL/β2-GLYCOPROTEIN I COMPLEX OCCURRING IN THE LIVING BODY

(76) Inventor: Eiji Matsuura, 20-801, Nishinocho 7-chome, Okayama-shi, Okayama (JP)

( * ) Notice: Subject to any disclaimer, the term of this patent is extended or adjusted under 35 U.S.C. 154(b) by 431 days.

(21) Appl. No.: 10/526,494

(22) PCT Filed: Sep. 5, 2003

(86) PCT No.: PCT/JP03/11388

§ 371 (c)(1), (2), (4) Date: Sep. 29, 2005

(87) PCT Pub. No.: WO2004/023141

PCT Pub. Date: Mar. 18, 2004

(65) Prior Publication Data

US 2006/0099644 A1 May 11, 2006

(30) Foreign Application Priority Data

Sep. 6, 2002 (JP) ............................ 2002-261366

(51) Int. Cl.
*G01N 33/53* (2006.01)

(52) U.S. Cl. ...................... 435/7.1; 435/7.2; 435/7.91; 435/7.92; 530/387

(58) Field of Classification Search .................. 435/7.1, 435/7.2, 7.91; 530/387
See application file for complete search history.

(56) References Cited

U.S. PATENT DOCUMENTS 5,900,359 A 5/1999 Matsuura et al.

FOREIGN PATENT DOCUMENTS

JP 7-306202 11/1995
WO 95/09363 4/1995

OTHER PUBLICATIONS

K. Kobayashi et al., "A specific ligand for β₂-glycoprotein I mediates autoantibody-dependent uptake of oxidized low density lipoprotein by macrophages", Journal of Lipid Research, vol. 42, pp. 697-709, 2001.
D. Steinberg et al., "Modification of Low-Density Lipoprotein that Increase its Atherogenicity", The New England Journal of Medicine, vol. 320, No. 14, pp. 915-924, Apr. 6, 1989.
H. C. Boyd et al., "Direct Evidence for a Protein Recognized by a Monoclonal Antibody against Oxidatively Modified LDL in Atherosclerotic Lesions from a Watanabe Heritable Hyperlipidemic Rabbit", American Journal of Pathology, vol. 135, No. 5, pp. 815-825, Nov. 1989.
Y. Nagano et al., "High density lipoprotein loses its effect to stimulate efflux of cholesterol from foam cells after oxidative modification", Proc. Natl. Acad. Sci., vol. 88, pp. 6457-6461, Aug. 1991.
M. Chang et al., "C-reactive protein binds to both oxidized LDL and apoptotic cells through recognition of a common ligand: Phosphorylcholine of oxidized phospholipids", PNAS, vol. 99, No. 20, pp. 13043-13048, Oct. 1, 2002.
H. Kamido et al., "Lipid ester-bound aldehydes among copper-catalyzed peroxidation products of human plasma lipoproteins", Journal of Lipid Research, vol. 36, pp. 1876-1886, 1995.
G. Hoppe et al., "Oxidation products of cholesteryl linoleate are resistant to hydrolysis is macrophages, form complexes with proteins, and are present in human atherosclerotic lesions", Journal of Lipid Research, vol. 38, pp. 1347-1360, 1997.
H. Kamido et al., "Identification of cholesterol-bound aldehydes in copper-oxidized low density liproprotein", FEBS Letters, vol. 304, No. 2 & 3, pp. 269-272, Jun. 1992.
J. Hulthe et al., "Relationship between C-reactive protein and intimamedia thickness in the carotid and femoral arteries and to antibodies against oxidized low-density lipoprotein in healthy men: the atherosclerosis and insulin resistance (AIR) study", Clinical Science, vol. 100, pp. 371-378, 2001.
M. Ryan et al., "Antibodies to oxidized lipoproteins and their relationship to myocardial infarction", Q J. Med, vol. 91, pp. 411-415, 1998.
C. Monaco et al., "Autoantibodies against oxidized low density lipoproteins in patient with stable angina, unstable angina or peripheral vascular disease", European Heart Journal, vol. 22, pp. 1572-1577, 2001.
E. Matsuura et al., "Anticardiolipin Antibodies Recognize β₂-Glycoprotein I Structure Altered by Interacting with an Oxygen Modified Solid Phase Surface", J. Exp. Med., vol. 179, pp. 457-462, Feb. 1994.
B. Bouma et al., "Adhesion mechanism of human β₂-glycoprotein I to phospholipids based on its crystal structure", The EMBO Journal, vol. 18, No. 19, pp. 5166-5174, 1999.
M. Hoshino et al., "Identification of the Phospholipid-binding Site of Human β₂-Glycoprotein I Domain V by Heteronuclear Magnetic Resonance", J. Mol. Biol., vol. 304, pp. 927-939, 1998.
D. Hong et al., "Flexible Loop of β₂-Glycoprotein I Domain V Specifically Interacts with Hydrophobic Ligands", Biochemistry, vol. 40, pp. 8092-8100, 2001.
Y. Hasunuma et al., "Involvement of β₂-glycoprotein I and anticardiolipin antibodies in oxidatively modified low-density lipoprotein uptake by macrophages", Clin. Exp. Immunol., vol. 107, pp. 569-573, 1997.
L. Kritharides et al., "A Method for Defining the Stages of Low-Density Lipoprotein Oxidation by the Separation of Cholesterol-and Cholesteryl Ester-Oxidation Products using HPLC", Analytical Biochemistry, vol. 213, pp. 79-89, 1993.

(Continued)

*Primary Examiner*—Long V. Le
*Assistant Examiner*—Changhwa J Cheu
(74) *Attorney, Agent, or Firm*—Wenderoth, Lind & Ponack, L.L.P.

(57) ABSTRACT

A complex having oxLDL bound covalently to β2-GPI can be used as a standard for measuring a β2-GPI/oxLDL complex in the living body thereby measuring the β2-GPI/oxLDL complex in the living body more accurately and strictly, and can be utilized to provide a new measurement method, detection method, kit etc.

14 Claims, 9 Drawing Sheets

OTHER PUBLICATIONS

J. George et al., "Induction of Early Atherosclerosis in LDL-Receptor-Deficient Mice Immunized with $\beta_2$-Glycoprotein I", Basic Science Reports, pp. 1108-1114, Sep. 15, 1998.

J. George et al., "Immunolocalization of $\beta_2$-Glycoprotein I (Apolipoprotein H) to Human Atherosclerotic Plaques" Basic Rapid Communication, pp. 2227-2229, May 4, 1999.

E. Matsuura et al., "Proteolytic cleavage of $\beta_2$-glycoprotein I: reduction of antigenicity and the structural relationship", International Immunology, vol. 12, No. 8, pp. 1183-1192, 2000.

P. Holvoet et al., "Oxidized LDL and Malondialdehyde-Modified LDL in Patients with Acute Coronary Syndromes and Stable Coronary Artery Disease", American Heart Association, pp. 1487-1494, Oct. 13, 1998.

K. Ichikawa et al., "A Chimeric Antibody with the Human $\gamma 1$ Constant Region as a Putative Standard for Assays to Detect IgG $\beta_2$Glycoprotein I-Dependent Anticardiolipin and Anti-$\beta_2$-Glycoprotein I Antibodies", Arthritis & Rheumatism, vol. 42, No. 11, pp. 2461-2470, Nov. 1999.

A. Ambrozic et al., "Anti-$\beta_2$-glycoprotein I antibodies in children with atopic dermatitis", International Immunology, vol. 14, No. 7, pp. 823-830, 2002.

Q. Liu et al., "$\omega$-Carboxyl variants of 7-ketocholesteryl esters are ligands for $\beta_2$-glycoprotein I and mediate antibody-dependent uptake of oxidized LDL by macrophages", Journal of Lipid Research, vol. 43, pp. 1486-1494, 2002.

G. M. Iverson et al., "The Orientation of $\beta$2GPI on the Plate is Important for the Binding of Anti-$\beta$2GPI Autoantibodies by ELISA", Journal of Autoimmunity, vol. 18, pp. 289-297, 2002.

E. Matsuura et al., "Anti-$\beta_2$-Glycoprotein I Autoantibodies and Atherosclerosis", Intern. Rev. Immunol., vol. 21, pp. 51-66, 2002.

S. Yasuda et al., "$\beta_2$-glycoprotein I deficiency: prevalence, genetic background and effects on plasma lipoprotein metabolism and hemostasis", Atherosclerosis, vol. 152, pp. 337-346, 2000.

J. George et al., "Oxidized low-density lipoprotein (Ox-LDL) but not LDL aggravates the manifestations of experimental antiphospholipid syndrome (APS)", Clin. Exp. Immunol., vol. 108, pp. 227-233, 1997.

Koike, "Antiphospholipid antibodies in arterial thrombosis", Annals of Medicine, vol. 32, No. Supp. 1, 2000, pp. 27-31.

E. Matsuura et al., "Anti-$\beta_2$-Glycoprotein I Autoantibodies and Atherosclerosis", International Reviews of Immunology, vol. 21, No. 1, pp. 51-66, Jan.-Feb. 2002.

Q. Liu et al., "$\omega$-Carboxyl variants of 7-ketocholesteryl esters are ligands for $\beta_2$-glycoprotein I and mediate antibody-dependent uptake of oxidized LDL by macrophages", Journal of Lipid Research, vol. 43, No. 9, pp. 1486-1495, Sep. 2002.

E. Matsuura et al., "Autoantibody-mediated atherosclerosis", Autoimmunity Reviews, vol. 1, No. 6, pp. 348-353, Aug. 25, 2002.

M. J. Cuadrado et al., "Antiphospholipid, anti-$\beta_2$-glycoprotein-I and anti-oxidized-low-density-lipoprotein antibodies in antiphospholipid syndrome", QJM - Monthly Journal of the Association of Physicians, vol. 91, No. 9, pp. 619-626, Sep. 1998.

FIG. 1
(A) I₂ vapor
oxLig-1 | 9-COOH-22KC
(B) Cof-22
oxLig-1 | 9-COOH-22KC
EY2C9
oxLig-1 | 9-COOH-22KC

US 7,455,976 B2

METHOD OF MEASURING OXIDIZED LDL/β2-GLYCOPROTEIN I COMPLEX OCCURRING IN THE LIVING BODY

This application is a U.S. national stage of International Application No. PCT/JP2003/011388 filed Sep. 5, 2003.

TECHNICAL FIELD

The present invention relates to a standard useful in measurement of "oxidized LDL (oxLDL)/β2-glycoprotein I (β2-GPI) complex" (β2-GPI/oxLDL complex) occurring in the living body and to a method of measuring the β2-GPI/oxLDL complex in vivo by using the standard.

BACKGROUND

First, abbreviations used in this specification will be described.
aPL: anti-phospholipid antibody
aCL: anti-cardiolipin antibody
APS: antiphospholipid syndrome
β2-GPI: β2-glycoprotein I
β2-GPI/oxLDL complex: complex consisting of oxLDL and β2-GPI
BSA: bovine serum albumin
CL: cardiolipin
$Cu^{2+}$-oxLDL: oxLDL oxidized with $CuSO_4$
DEAE: diethylaminoethyl
EDTA: ethylenediaminetetraacetic acid
ELISA: enzyme-linked immunosorbent assay
HRP: horseradish peroxidase
LDL: low-density lipoprotein
MDA: malondialdehyde
OD: optical density
oxLDL: oxidized LDL
oxLig-1: 7-ketocholesteryl-9-carboxynonanoate; 9-oxo-9-(7-ketocholest-5-en-3β-yloxy)nonanoic acid (IUPAC)
oxLig-2: 7-ketocholesteryl-12-carboxy(keto)dodecanoate
PAPS: primary antiphospholipid syndrome
PBS: phosphate buffered saline
PL (PLs): phospholipid(s)
SLE: systemic lupus erythematosus
TBARS: thiobarbituric acid reactive substance
TLC: thin layer chromatography
9-COOH-22KC: 7-ketocholesteryl-13-carboxytridecanoate; 13-oxo-13-(7-ketocholest-5-en-3β-yloxy)tridecanoic acid It is known that β2-GPI is a major antigen which is recognized by "phospholipid antibody" occurring in patients with APS, and binds specifically to oxLDL but not to non-oxidized (native) LDL. WO 95/9363 discloses a method of measuring oxLDL by using such ability of β2-GPI to bind specifically to oxLDL, its applied kit for diagnosis of arteriosclerotic diseases, etc. Further, J. Lipid Res., 42, pp. 697-709 (2001) [reference 7] discloses that β2-GPI recognizes the structural part of oxLig-1 in oxLDL and binds thereto.

oxLDL forms a complex with β2-GPI (β2-GPI/oxLDL complex) in the living body, and by measuring this complex occurring in the living body, various diseases can be detected. As a standard for measuring this complex occurring in the living body, $Cu^{2+}$-oxLDL and β2-GPI which were contacted with each other without pre-incubation have been conventionally used.

A standard for measuring the hardly dissociable β2-GPI/oxLDL complex occurring in the living body is desirably the same as, or as similar as possible to, the standard for measuring the complex occurring in the living body. However, a mode of bonding between oxLDL and β2-GPI, etc., in the β2-GPI/oxLDL complex occurring in the living body and in the β2-GPI/oxLDL complex used conventionally as the standard have not been known.

DISCLOSURE OF THE INVENTION

The present invention relates to a standard useful for measurement of the β2-GPI/oxLDL complex occurring in the living body, as well as a method of measuring the β2-GPI/oxLDL complex in vivo by using the standard.

The present inventors have studied a mode of bonding between oxLDL and β2-GPI in the β2-GPI/oxLDL complex occurring in the living body, and as a result, we have surprisingly found that a majority of the complexes form a covalent bonding or a stronger bonding than at least electrostatic bonding force. On the other hand, the present inventors have found that when the conventionally used standard (that is, oxLDL and β2-GPI contacted with each other without pre-incubation) is subjected to measurement, the bonding between oxLDL and β2-GPI in this complex is a mere electrostatic bonding.

The conventional standard can be used in measurement of the β2-GPI/oxLDL complex occurring in the living body. For carrying out more accurate and strict measurement, however, the standard is desirably as similar as possible to the complex occurring in the living body, as described above.

On the basis of the foregoing new finding, the present inventors have successfully provided a novel standard for measuring β2-GPI/oxLDL complex, a method of measuring β2-GPI/oxLDL complex by using the standard, a method of detecting a disease by using the measurement method, and a kit for measuring β2-GPI/oxLDL complex by using the standard, and the present invention has been thereby completed.

Further, the present inventors have also paid attention to the fact that an antigen used in measurement of "antibody recognizing β2-GPI/oxLDL complex" (autoantibody) occurring in the living body is also desirably as similar as possible to the β2-GPI/oxLDL complex occurring in the living body, and have successfully provided a novel antigen for measuring the "antibody recognizing β2-GPI/oxLDL complex", a method of measuring the "antibody recognizing β2-GPI/oxLDL complex" by using the antigen, a method of detecting a disease by using the measurement method, a solid phase having the antigen immobilized thereon, and a kit for measuring the "antibody recognizing β2-GPI/oxLDL complex" by using the solid phase, and the present invention has been thereby completed.

That is, the present invention provides a standard for measuring a β2-GPI/oxLDL complex in a sample, which comprises a complex having oxLDL bound covalently to β2-GPI as an ingredient (this standard is referred to hereinafter as standard 1 of the present invention).

The present invention also provides a standard for measuring a β2-GPI/oxLDL complex in a sample, which comprises "β2-GPI/oxLDL complex obtainable by incubating oxLDL and β2-GPI under the conditions of 37° C. and pH 7.4 for 16 hours" as an ingredient (this standard is referred to hereinafter as standard 2 of the present invention). The "β2-GPI/oxLDL complex obtainable by incubating oxLDL and β2-GPI under the conditions of 37° C. and pH 7.4 for 16 hours" in the standard 2 of the present invention preferably has the following properties (a) and (b):

(a) oxLDL and β2-GPI constituting the complex are substantially not dissociated even in the coexistence of 100 U/ml heparin, and (b) oxLDL and β2-GPI constituting the complex are substantially not dissociated even in the coexistence of 10 mM MgCl$_2$.

The "sample" subjected to measurement using the standard of the present invention is preferably a sample derived from a living body. This "sample derived from a living body" is preferably blood.

Hereinafter, both standards 1 and 2 of the present invention are collectively referred to simply as "standard of the present invention".

Further, the present invention provides a method of measuring a β2-GPI/oxLDL complex in a sample, which comprises using the standard of the present invention (this method is referred to hereinafter as measurement method 1 of the present invention). The measurement method 1 of the present invention preferably comprises at least a step of covalently binding "oxLDL" to "β2-GPI" in a sample. Preferably the method also comprises at least a step of previously incubating "oxLDL" and "β2-GPI" in a sample under the condition of pH 3 to 9. Preferably the method also comprises at least a step of dissociating "complex having 'oxLDL' bound electrostatically to 'a protein, a polypeptide, an amino acid, an aminosugar or an aminolipid'" in a sample.

Further, the present invention provides a method of detecting a disease, which comprises measuring a β2-GPI/oxLDL complex in a sample by using the measurement method 1 of the present invention and correlating the measured "complex in the sample" with a disease (this method is referred to hereinafter as detection method 1 of the present invention). The disease detected by the detection method 1 of the present invention is preferably selected from the group consisting of APS, thrombosis, arterial thrombosis, venous thrombosis, pregnancy morbidity, renal disease, arteriosclerosis (cerebral infarction, myocardial infarction etc.) and diabetes.

Further, the present invention provides a kit for measuring a β2-GPI/oxLDL complex in a sample, which comprises the standard of the present invention as a constituent ingredient (this kit is referred to hereinafter as kit 1 of the present invention). Preferably the kit 1 of the present invention further comprises "antibody recognizing the 'oxLDL/β2-GPI complex'" as a constituent ingredient. Preferably the kit 1 of the present invention is used in detection of a disease.

Further, the present invention provides an antigen for measuring "antibody recognizing the β2-GPI/oxLDL complex" in a sample, which comprises the "complex having oxLDL bound covalently to β2-GPI" as an ingredient (this antigen is referred to hereinafter as antigen 1 of the present invention).

The present invention also provides an antigen for measuring "antibody recognizing the β2-GPI/oxLDL complex" in a sample, which comprises the "β2-GPI/oxLDL complex obtainable by incubating oxLDL and β2-GPI under the conditions of 37° C. and pH 7.4 for 16 hours" as an ingredient (this antigen is referred to hereinafter as antigen 2 of the present inventions. The "β2-GPI/oxLDL complex obtainable by incubating oxLDL and β2-GPI under the conditions of 37° C. and pH 7.4 for 16 hours" in the antigen 2 of the present invention preferably has the following properties (a) and (b):
(a) oxLDL and β2-GPI constituting the complex are substantially not dissociated even in the coexistence of 100 U/ml heparin, and
(b) oxLDL and β2-GPI constituting the complex are substantially not dissociated even in the coexistence of 10 MM MgCl$_2$.

Hereinafter, antigens 1 and 2 of the present invention are collectively referred to simply as "antigen of the present invention".

Further, the present invention provides a method of measuring "antibody recognizing the β2-GPI/oxLDL complex" in a sample, which comprises using the antigen of the present invention (this method is referred to hereinafter as measurement method 2 of the present invention).

Further, the present invention provides a method of detecting a disease, which comprises measuring "antibody recognizing the β2-GPI/oxLDL complex" in a sample by using the measurement method 2 of the present invention, and correlating the measured "antibody in the sample" with a disease (this method is referred to hereinafter as detection method 2 of the present invention). The disease detected by the detection method 2 of the present invention is preferably selected from the group consisting of APS, thrombosis, arterial thrombosis, venous thrombosis, pregnancy morbidity, renal disease, arteriosclerosis (cerebral infarction, myocardial infarction etc.) and diabetes.

The present invention also provides a solid phase having the antigen of the present invention immobilized thereon (this solid phase is referred to hereinafter as solid phase of the present invention).

Further, the present invention provides a kit for measuring "antibody recognizing the β2-GPI/oxLDL complex" in a sample, which comprises the solid phase of the present invention as a constituent ingredient (this kit is referred to hereinafter as kit 2 of the present invention). Preferably the kit 2 of the present invention further comprises a substance binding to "antibody recognizing the β2-GPI/oxLDL complex" as a constituent ingredient. Preferably the kit 2 of the present invention is used in detection of a disease.

The present invention also provides a method of measuring an immune complex in a sample, which comprises using "antibody recognizing 132-GPI" and/or "antibody recognizing LDL" and an anti-IgG antibody (this method is referred to hereinafter as measurement method 3 of the present invention).

BRIEF DESCRIPTION OF THE DRAWINGS

FIG. 1 is a graph showing ligand blotting analysis of two ω-carbdxylmutants (oxLig-1 and 9-COOH-22KC) of oxysterol ester. The ligand developed on a TLC plate was stained with I$_2$ vapor (A), and the ligand blotting was conducted by using anti-β2-GPI antibody (Cof-22 (B) and EY2C9 (C)).

(A) TBARS in LDL (treated with 5 μM CuSO$_4$ for the time shown in the graph) was measured.

(B) The β2-GPI/oxLDL complex was formed by incubating Cu$^{2+}$-oxLDL (2.5 μg/ml in terms of apoB) together with β2-GPI (0 μg/ml (white circle), 25 μg/ml (black circle)) in wells and subjected to ELISA. ELISA in the coexistence of 25 μg/ml β2-GPI was also conducted in the presence of heparin (100 U/ml; black square) or MgCl$_2$ (10 mM; black lozenge).

(C) The β2-GPI/oxLDL complex was formed by incubating oxLDL12h (100 μg/ml) together with β2-GPI (100 μg/ml) under the condition of 4° C. (dotted line) or 37° C. (solid line) for the time shown in the graph and then detected by ELISA. ELISA was also conducted in the absence of heparin and MgCl$_2$ (white circle) or in the presence of heparin (100 U/ml; black square) or MgCl$_2$ (10 mM; black lozenge).

(D) The β2-GPI/oxLDL complex was formed by incubating LDL (100 μg/ml) and β2-GPI (100 μg/ml) simultaneously in a process of oxidation with Cu$^{2+}$ (5 μM) at 37° C., and the β2-GPI/oxLDL complex (2.5 μg/ml in terms of apoB) was detected by ELISA. ELISA was conducted in the presence of heparin (100 U/ml; black square) or in the presence (10 mM; black lozenge) or absence (white circle) of MgCl$_2$. The data are shown by the mean±SD of 3 samples.

Figure 4:
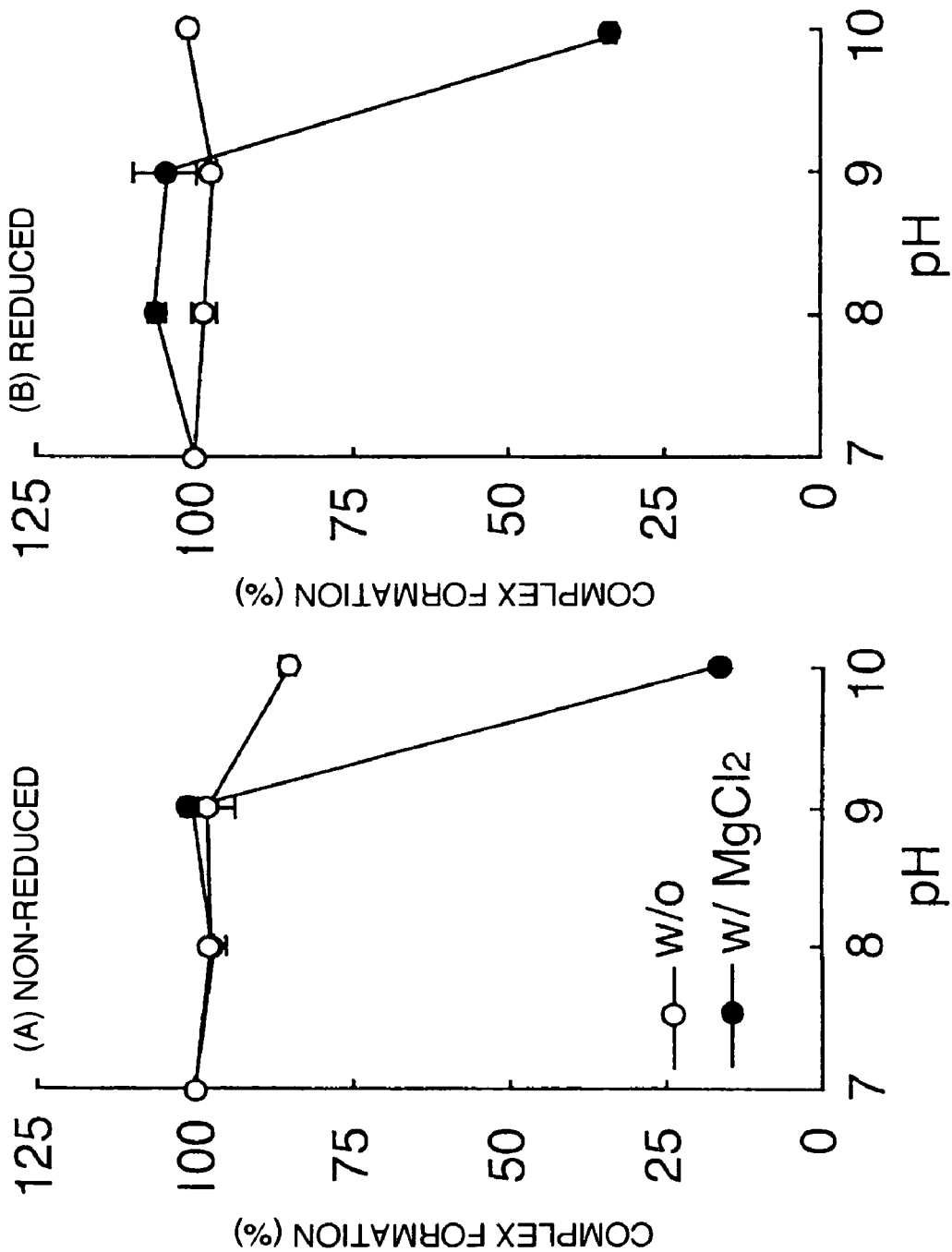

FIG. 4 is a graph showing the stability of the oxLDL12h/β2-GPI16h complex and the complex reduced with NaCNBH$_3$ under varying pH conditions The oxLDL12h/β2-GPI16h complex (100 μg/ml in terms of apoB) was reduced by treatment with 200 mM NaCNBH$_3$ at pH 7.4 for 16 hours in PBS. The unreduced or reduced complex was incubated at 37° C. for 16 hours in the presence or absence of 10 MM MgCl$_2$ under the pH condition shown in the graph. The β2-GPI/oxLDL complex in this preparation containing 300 ng/ml LDL (in terms of apoB) was measured by ELISA. The data are shown by the mean±SD of 3 samples.

Figure 5:
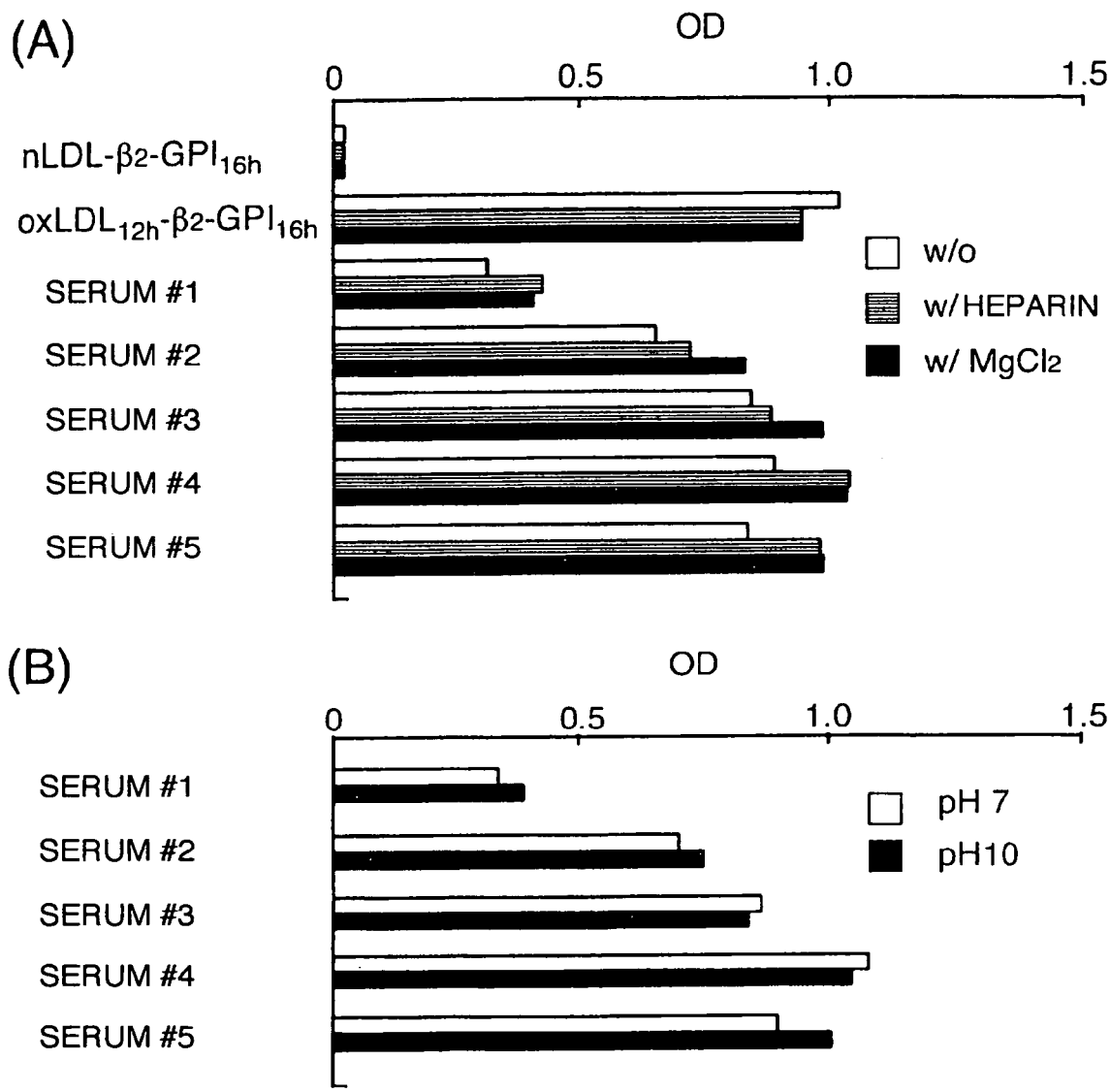

FIG. 5 is a graph showing β2-GPI/oxLDL complex present in serum from patients.

(A) Native LDL (nLDL)/β2-GPI16h (reaction mixture wherein native LDL and β2-GPI had been incubated at 37° C. for 16 hours; negative control) (300 ng/ml in terms of apoB), oxLDL12h/β2-GPI16h (300 ng/ml) or a 100-fold dilution of β2-GPI/oxLDL complex-positive serum was incubated in the presence or absence of heparin (100 U/ml) or MgCl$_2$ (10 mM).

(B) β2-GPI/oxLDL complex-positive serum was pre-incubated at pH 10, 37° C. for 16 hours in the presence of MgCl$_2$ (10 mM) and subjected to ELISA. The data are shown by the mean of two samples.

Figure 6:
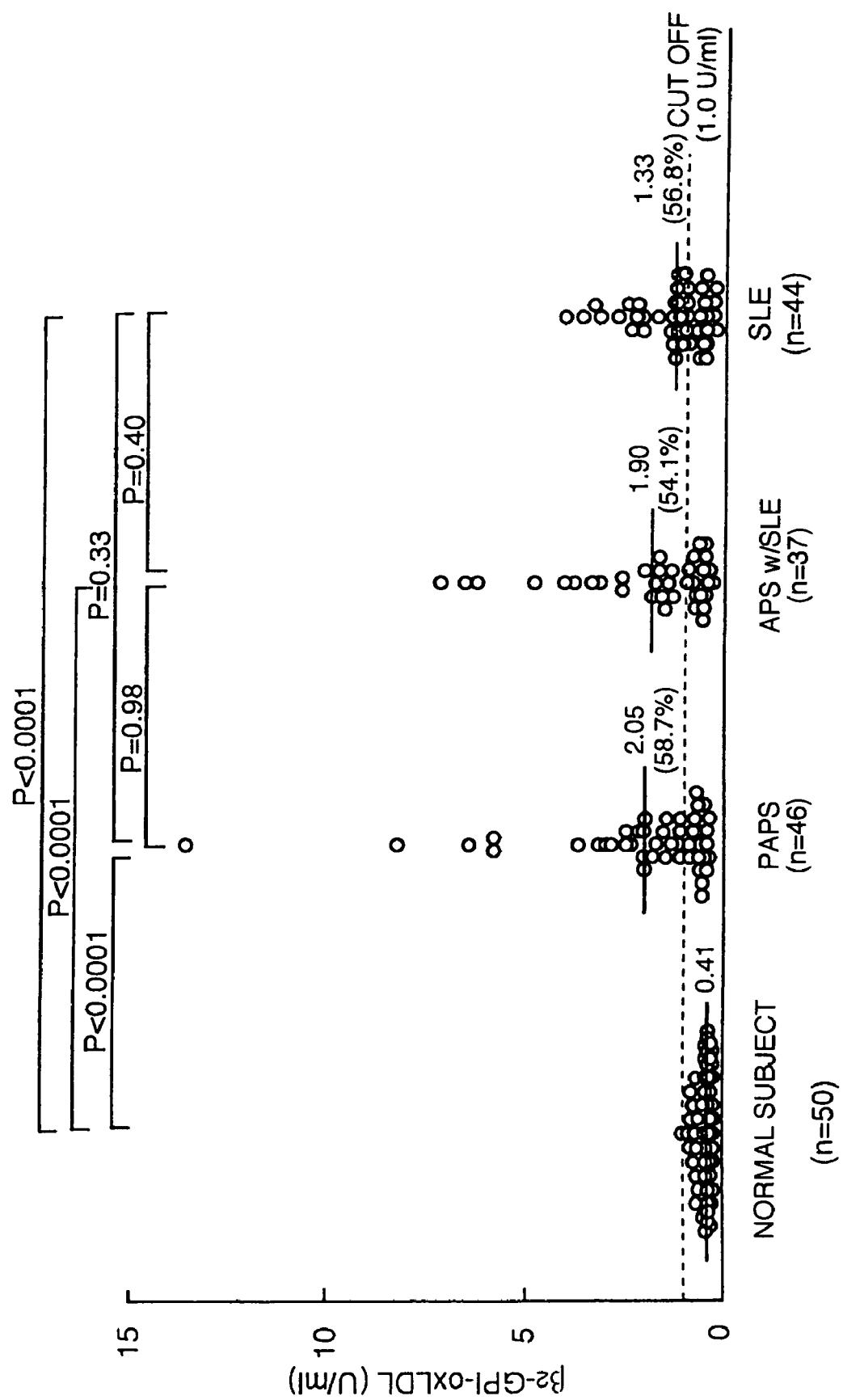

FIG. 6 is a graph showing the serum level of β2-GPI/oxLDL complex detected by ELISA.

Serums collected from healthy persons and patients with primary APS (PAPS), APS accompanied by SLE (secondary APS), or SLE not accompanied by APS were diluted 100-fold to detect β2-GPI/oxLDL complex. The cut-off value (1 U/ml) was regulated so as to be 3 times as high as the standard deviation of the mean of 50 healthy persons. Number in the graph shows the mean of each group.

Figure 7:
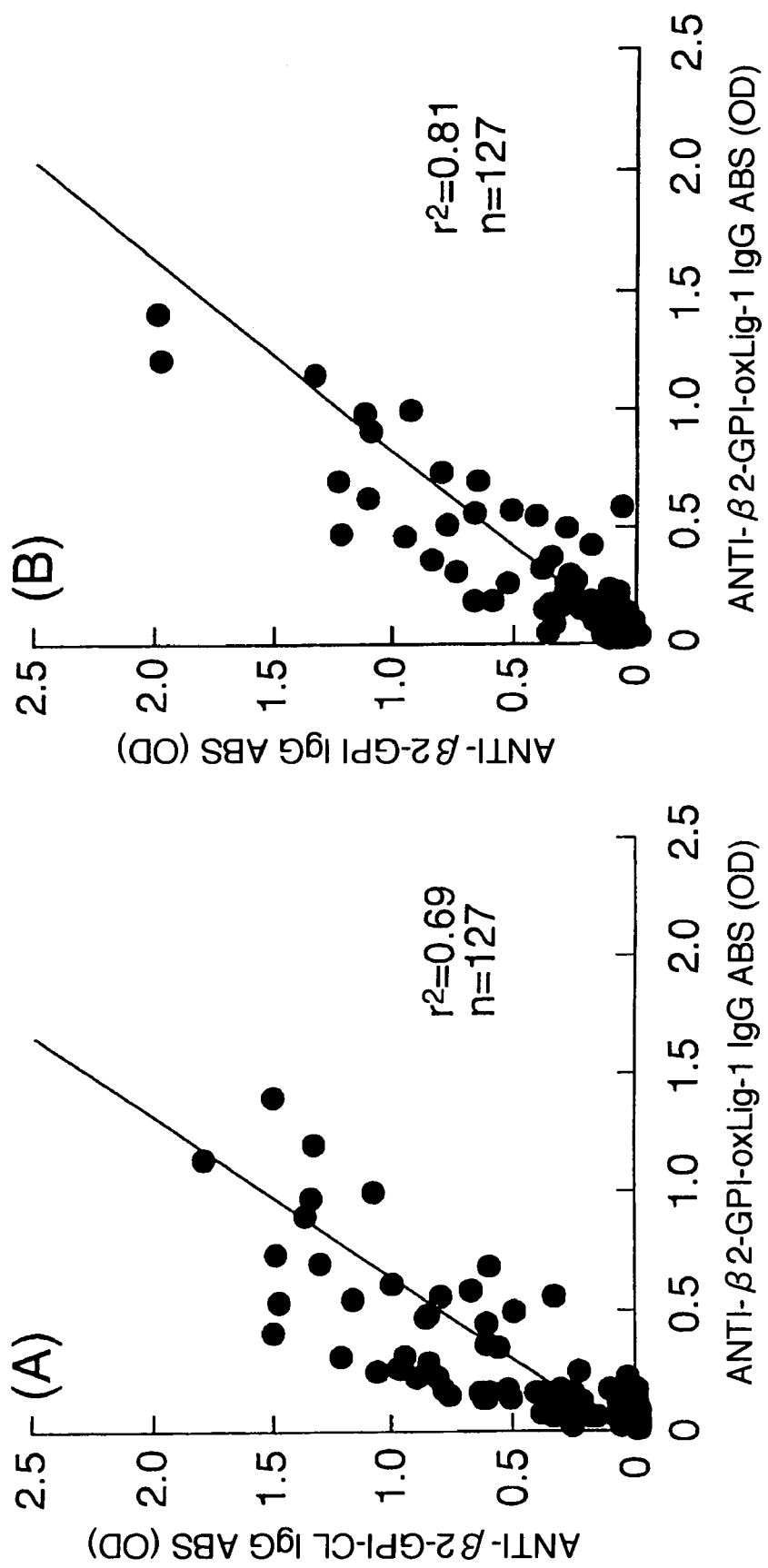

FIG. 7 is a graph showing the relationship among the antibody titers of β2-GPI-related IgG antibodies detected in 3 different ELISA systems.

(A) Relationship between "β2-GPI-dependent IgG aCL (anti-β2-GPI/CL IgG antibody)" and "anti-β2-GPI/oxLig-1 IgG antibody".

(B) Relationship between "anti-β2-GPI IgG antibody (detected by ELISA using a polyoxidized plate coated with β2-GPI)" and "anti-β2-GPI/oxLig-1 IgG antibody".

Figure 8:
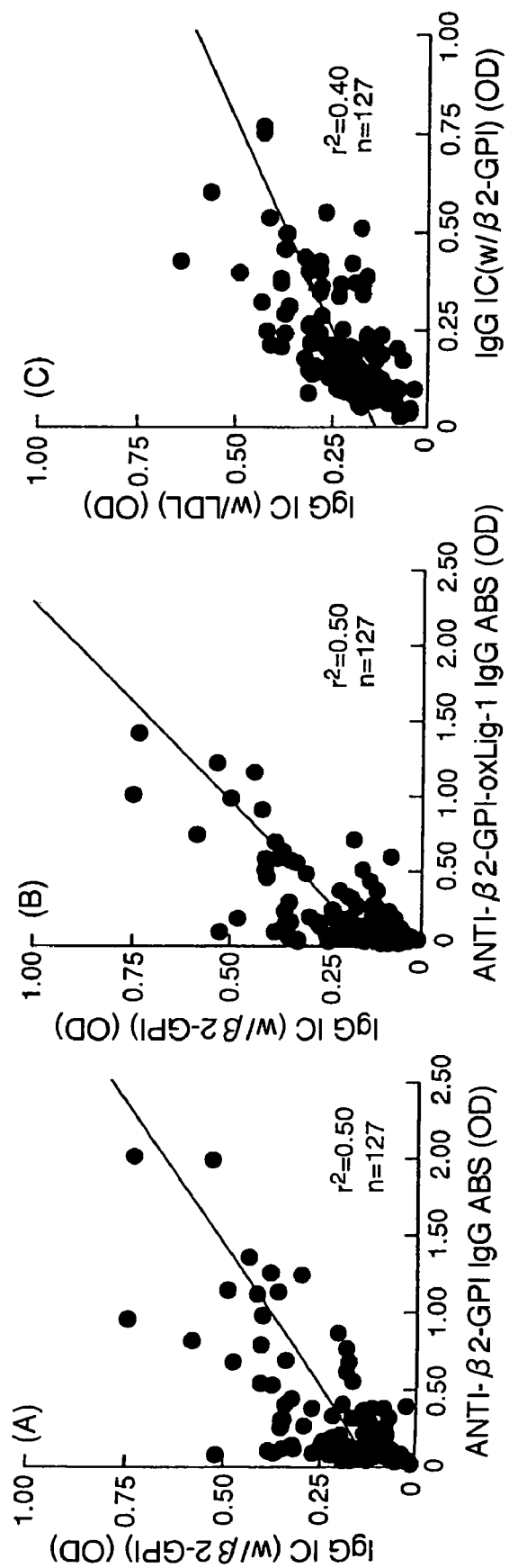

FIG. 8 is a graph showing the relationship between IgG antibody titer and IgG immune complex level.

(A) Relationship between "anti-β2-GPI IgG antibody" and "β2-GPI/IgG immune complex (IC)".

(B) Relationship between "anti-β2-GPI/oxLig-1 IgG antibody" and "LDL/IgG immune complex".

(C) Relationship between "β2-GPI/IgG immune complex" and "LDL/IgG immune complex".

Figure 9:
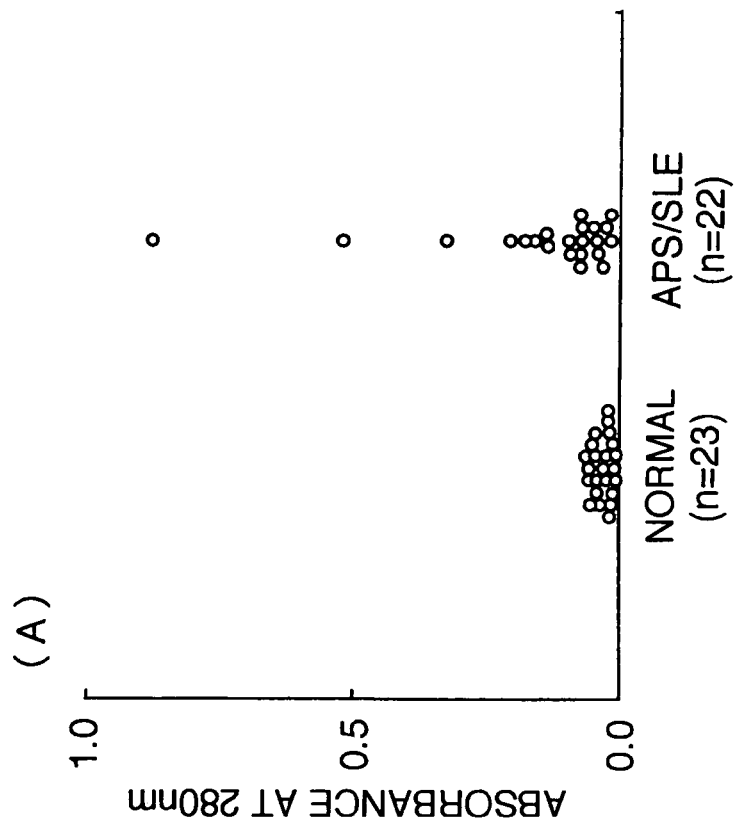

FIG. 9 is a graph showing the detection result of "antibody recognizing β2-GPI/oxLDL complex" by ELISA. (A) is a graph showing the serum level of the antibody recognizing β2-GPI/oxLDL complex. (B) shows the relationship between the "antibody recognizing β2-GPI/oxLDL complex" and the "anti-β2-GPI IgG antibody".

BEST MODE FOR CARRYING OUT THE INVENTION

Hereinafter, the mode for carrying out the invention will be described.

Standard of the Present Invention

<1>-1 Standard 1 of the Present Invention

The standard 1 of the present invention is a standard for measuring a β2-GPI/oxLDL complex in a sample, which comprises complex having oxLDL bound covalently to β2-GPI.

The "oxLDL" constituting the standard 1 of the present invention can be prepared by oxidizing LDL. Although the method of oxidization is not particularly limited, a method that involves incubation with Cu$^{2+}$ can be mentioned as a preferable method. For example, LDL can be oxidized by incubating LDL with about 5 μM CuSO$_4$ at a temperature of about 37° C. In this case, the oxidation reaction can be terminated by adding a chelating agent such as EDTA. For specific examples of this method, reference is made to the Examples shown later.

The "β2-GPI" constituting the standard 1 of the present invention can be obtained from serum etc. in mammals or can be produced by genetic engineering techniques. The origin of "β2-GPI" is not particularly limited, but "β2-GPI" is preferably derived from the same animal species as that of an animal from which the "sample" subjected to measurement was collected. For example, when the sample subjected to measurement is human serum, human-derived β2-GPI is preferably used.

The standard 1 of the present invention comprises, as an ingredient, the complex having "oxLDL" bound covalently to the "β2-GPI". The method of covalently binding the two is not particularly limited, and can be suitably selected from known techniques.

By binding "oxLDL" and "β2-GPI" covalently to each other in this manner, the two forms a hardly dissociable complex. The "complex having oxLDL bound covalently to β2-GPI" in the standard 1 of the present invention is used as a standard for measuring the D2-GPI/oxLDL complex in a sample.

The term "measurement" in this specification is a concept encompassing not only quantitative measurement of a certain substance but also qualitative detection (detection of the presence or absence of a certain substance).

The term "standard" in this specification means "standard substance" used in measuring a certain substance. That is, when quantitative or qualitative measurement of a certain substance A is to be conducted, substance A (standard substance) serving as standard is necessary. For example, when substance A in a sample is quantitatively measured by using OD, substance A (standard substance) prepared at a predetermined concentration is measured for its OD, and the OD value of the sample is compared with the OD value of this standard substance, whereby the concentration of substance A in the sample can be determined. Further, when the presence or absence of substance A in a sample is judged (that is, when substance A is qualitatively measured), the presence or absence of substance A in the sample can be judged (substance A can be qualitatively measured) by using as an indicator the presence or absence of a substance having the same physicochemical properties and biological properties (for example, antigenicity etc.) as those of substance A (standard substance) as standard. The "standard substance" used in such measurement is a typical example of the "standard" in this specification.

The standard 1 of the present invention may further contain other ingredients insofar as the "complex having oxLDL bound covalently to β2-GPI" is contained as an ingredient. The "other ingredients" used herein are not particularly limited insofar as they do not adversely affect the physicochemical properties and biological properties (for example antigenicity etc.) of the "complex having oxLDL bound covalently to β2-GPI" itself, and do not inhibit the functions of the complex as standard. As used herein, the "other ingredients" are exemplified by an excipient, a buffer agent, a stabilizer, a preservative etc. used in preparation of usual reagents.

The form of the standard 1 of the present invention is not particularly limited insofar as the standard can be formed as desired for use, and for example the standard can be used in forms such as a dissolved form, a frozen form and a lyophilized form. This product can be charged into a suitable container such as an ampoule, vial, syringe or bottle and can be distributed as such or stored, and can be used as the standard for measurement.

<1>-2 Standard 2 of the Present Invention

The standard 2 of the present invention is the standard for measuring β2-GPI/oxLDL complex in a sample, which comprises "β2-GPI/oxLDL complex obtainable by incubating oxLDL and β2-GPI under the conditions of 37° C. and pH 7.4 for 16 hours" as an ingredient.

A description of "oxLDL" and "β2-GPI" in the standard 2 of the present invention is the same as described above in the "standard 1 of the present invention".

The standard 2 of the present invention comprises, as an ingredient, the β2-GPI/oxLDL complex obtainable by incubating oxLDL and β2-GPI under the conditions of 37° C. and pH 7.4 for 16 hours. The term "obtainable" means that the β2-GPI/oxLDL complex as the ingredient of the standard 2 of the present invention is not limited to the "complex actually obtained by incubating oxLDL and β2-GPI under the conditions of 37° C. and pH 7.4 for 16 hours" but may include the complex obtained by a method different therefrom. Accordingly, when the β2-GPI/oxLDL complex obtained by a different method is evaluated to be equal as substance to the "β2-GPI/oxLDL complex actually obtained by incubating oxLDL and β2-GPI under the conditions of 37° C. and pH 7.4 for 16 hours", the β2-GPI/oxLDL complex obtained by the different method can also be used as the ingredient of the standard 2 of the present invention.

The ingredient of the standard 2 of the present invention, that is, the "complex obtainable by incubating oxLDL and β2-GPI under the conditions of 37° C. and pH 7.4 for 16 hours" preferably has the following properties (a) and (b):

(a) oxLDL and β2-GPI constituting the complex are substantially not dissociated even in the coexistence of 100 U/ml heparin, and (b) oxLDL and β2-GPI constituting the complex are substantially not dissociated even in the coexistence of 10 MM $MgCl_2$.

The β2-GPI/oxLDL complex having the properties (a) and (b) can be obtained by incubating at least oxLDL and β2-GPI under the conditions of 37° C. and pH 7.4 for 16 hours. However, the β2-GPI/oxLDL complex which can be used as the ingredient of the standard 2 of the present invention is not limited to the complex actually obtained by this method, but may be the complex obtained by a method different therefrom, as described above.

The standard 2 of the present invention makes use of such β2-GPI/oxLDL complex as a standard for measuring the β2-GPI/oxLDL complex in a sample.

The standard 2 of the present invention, similar to the standard 1 of the present invention, may contain other ingredients insofar as such β2-GPI/oxLDL complex is contained as an ingredient, and a description and examples of the "other ingredients" are the same as described above in the "standard 1 of the present invention".

A description etc. of the form etc. of the standard 2 of the present invention is also the same as described above in the "standard 1 of the present invention".

The sample subjected to measurement using the standard of the present invention is not particularly limited insofar as it requires measurement of β2-GPI/oxLDL complex. The sample may not be purified for β2-GPI/oxLDL complex. The sample is preferably a sample derived from a living body, and the sample derived from a living body is exemplified specifically by blood (which is used in this specification as a concept including serum and plasma). The blood may be used as it is, may be diluted, or maybe processed to such an extent that the β2-GPI/oxLDL complex in a sample is not adversely affected.

<2> Measurement Method 1 of the Present Invention

The measurement method 1 of the present invention is a method of measuring β2-GPI/oxLDL complex in a sample, which comprises using the standard of the present invention.

As used herein, the "standard of the present invention" may be either standard 1 or 2 of the present invention. Its description is as described above.

How the measurement method 1 of the present invention is specifically carried out is not limited insofar as the standard of the present invention is used. Specific methods are exemplified by immunological measurement techniques using e.g. antibody (ELISA [sandwich method, competitive method, inhibition method etc.], immunoblotting, agglutination method etc.).

It has been found by the present inventors that a majority of bonds formed between oxLDL and β2-GPI in β2-GPI/oxLDL complexes occurring in the living body are covalent bonds or stronger bonds than at least electrostatic binding force, and some bonds are electrostatic bonds. It has been confirmed by the present inventors that the complex having a covalent bond and the complex having an electrostatic bond are slightly different from each other in respect of physicochemical properties and biological properties (for example antigenicity etc.).

Accordingly, previous formation of a covalent bond between oxLDL and β2-GPI in every "β2-GPI/oxLDL complex formed by electrostatic bonding" present in a sample is preferable in that every complex (covalently bound complex and electrostatically bound complex) present in the sample can be measured more accurately. That is, the measurement method 1 of the present invention preferably comprises at least a step of covalently binding "oxLDL" to "β2-GPI" in a sample. A description of the covalently binding is the same as described above in the "standard 1 of the present invention".

As previously described in the "standard 2 of the present invention", oxLDL and β2-GPI are incubated under the condition of pH 3 to 9 (for example, pH 7.4), whereby a bond having the following properties (a) and (b) can be formed between oxLDL and β2-GPI.

(a) oxLDL and β2-GPI constituting the complex are substantially not dissociated even in the coexistence of 100 U/ml heparin, and
(b) oxLDL and β2-GPI constituting the complex are substantially not dissociated even in the coexistence of 10 MM $MgCl_2$.

Accordingly, the conversion of the bond in every "β2-GPI/oxLDL complex formed by electrostatic bonding" present in a sample into the bond having the properties (a) and (b) is preferable in that every complex in the sample (that is, the complex having the bond with the properties (a) and (b) and the complex having an electrostatic bond) can be measured more accurately. That is, the measurement method 1 of the present invention preferably comprises at least a step of previously incubating "oxLDL" and "β2-GPI" in a sample under the condition of pH 3 to 9. Specifically, the pH value is about 7.4.

The bond having the properties (a) and (b) is considered due to formation of Schiff base, and this reaction proceeds with an acid catalyst. Accordingly, the pH value during incubation is preferably neutral to acidic. However, strongly acidic conditions cause protein denaturation and are thus not preferable.

Although the incubation temperature is not particularly limited insofar as it is to such an extent that the functions of oxLDL and β2-GPI are not lost, the incubation temperature is for example 37° C. or thereabout. The incubation time is not particularly limited either, and can be suitably established by those skilled in the art. Generally, the above bond can be formed more completely as the incubation time is increased.

Previous dissociation of oxLDL from β2-GPI in every "β2-GPI/oxLDL complex formed by electrostatic bonding" present in a sample is preferable in that only the complex having a covalent bond or the bond having the properties (a) and (b), present in the sample, can be measured more accurately. That is, the measurement method 1 of the present invention preferably comprises at least a step of dissociating "a complex having 'oxLDL' bound electrostatically to 'a protein, a polypeptide, an amino acid, an aminosugar or an aminolipid'" in a sample. The dissociation method, conditions etc. are not particularly limited insofar as the electrostatically bound complex only is dissociated, while the complex having a covalent bond or the bond with the properties (a) and (b) is not dissociated; for example, there is a method that involves incubating the complex in the presence of heparin or a salt such as $MgCl_2$, $CaCl_2$ or the like. The concentration of these substances, the incubation temperature, the incubation time etc. can be suitably determined by those skilled in the art in such a range that while the electrostatically bound complex only is dissociated, the complex having a covalent bond or the bond with the properties (a) and (b) is not dissociated. The incubation temperature is for example 37° C. or thereabout. Generally, the complex can be dissociated into its components more completely as the incubation time is increased.

The meaning of the "sample" is the same as described in the "standard of the present invention".

<3> Detection Method 1 of the Present Invention

The detection method 1 of the present invention is a method of detecting a disease, which comprises measuring a β2-GPI/oxLDL complex in a sample by using the measurement method 1 of the present invention and correlating the measured "complex in the sample" with a disease.

In the detection method 1 of the present invention, the β2-GPI/oxLDL complex in a sample is first measured by the measurement method 1 of the present invention. A description of the measurement method 1 of the present invention is as described above. The "sample" used herein is not particularly limited insofar as it is derived from the living body of an animal subjected to detection of a disease, and specifically blood etc. can be mentioned. Other description of the "sample" is the same as described above in the "standard of the present invention".

In the detection method 1 of the present invention, the "β2-GPI/oxLDL complex in the sample" measured by using the measurement method 1 of the present invention is then correlated with a disease to detect the disease.

As described above, the term "measurement" in this specification is a concept encompassing not only quantitative measurement but also qualitative detection (detection of the presence or absence). Accordingly, the "measured 'β2-GPI/oxLDL complex in the sample'" as used herein may be measured for its "amount" in the sample (quantitative measurement result) or its "presence or absence" in the sample (qualitative measurement result). The amount may be either an amount (observed value) determined from a calibration curve prepared using the present standards of known concentrations, a relationship etc. or a ratio (relative value) relative to a value of healthy animals (animals having no disease).

The amount of the "β2-GPI/oxLDL complex" is increased by a certain disease so that when the amount of the complex in a sample is higher than that of a healthy person, the sample can be correlated with "contraction of the disease" or "high possibility of contraction of the disease". When the amount of the complex in the sample is equal to that of a healthy person, the sample can be correlated with "absence of contraction of the disease" or "low possibility of contraction of the disease".

The detection method 1 of the present invention can detect not only contraction of a disease but also the severity of the contracted disease. For example, when the amount of the complex in a sample from a certain person tends to be increased in periodic measurement, the sample can be correlated with "progress of the disease" or "high possibility of progress of the disease". On the other hand, when the amount of the complex measured tends to be decreased, the sample can be correlated with "tendency to ameliorate the disease" or "high possibility of tendency to ameliorate the disease". When the amount of the complex measured tends to be constant, the sample can be correlated with "no change in the severity of the disease (or no change in health)" or "high possibility of no change in the severity of the disease (or high possibility of no change in health)".

The "disease" detected by the detection method 1 of the present invention is preferably selected from the group consisting of APS, thrombosis, arterial thrombosis, venous thrombosis, pregnancy morbidity, renal disease, arteriosclerosis (cerebral infarction, myocardial infarction etc.) and diabetes.

<4> Kit 1 of the Present Invention

The kit 1 of the present invention is a kit for measurement of a β2-GPI/oxLDL complex in a sample, which comprises the standard of the present invention as a constituent ingredient. The "standard of the present invention" used herein may be either standard 1 or 2 of the present invention. Its description is as described above.

The kit 1 of the present invention may contain other constituent ingredients insofar as it contains the standard of the present invention as a constituent ingredient. Preferably the kit further contains "antibody recognizing β2-GPI/oxLDL complex" as a constituent ingredient.

The "antibody recognizing β2-GPI/oxLDL complex" is not particularly limited either, and can be exemplified by, for example, an anti-β2-GPI autoantibody WB-CAL-1 (IgG2a, κ) and a mouse monoclonal anti-human apoB100 antibody ID2 (IgG).

The "antibody recognizing β2-GPI/oxLDL complex" is preferably labeled with a labeling substance in order to facilitate detection.

Instead of labeling the "antibody recognizing β2-GPI/oxLDL complex" itself, a substance binding to the "antibody recognizing β2-GPI/oxLDL complex" may be labeled.

The labeling substance used in such labeling includes enzymes (peroxidase, alkali phosphatase, β-galactosidase, luciferase, acetylcholine esterase etc.), fluorochromes (fluorescein isothiocyanate (FITC) etc.), chemoluminescent substances (luminol etc.), biotin, avidin (including streptoavidin) etc., but is not particularly limited insofar as it can be used in usual labeling of protein. The labeling method can be selected suitably from known methods suitable for the labeling substance, for example a glutaraldehyde method, periodate crosslinking method, maleimide crosslinking method, carbodiimide method and activated ester method [see "Tanpakushitsu No Kagaku" (Protein Chemistry), Third Volume, published in 1987 by TOKYO KAGAKU DOZIN CO., LTD.]. For example, when biotin is used as the labeling substance, a method of using a hydrazide derivative of biotin (see Avidin-Biotin Chemistry: A Handbook, pp. 57-63, published in 1994 by PIERCE CHEMICAL COMPANY) can be used, or when fluorescein isothiocyanate is used, the labeling method can be selected from methods described in Japanese Published Examined Patent Application No. 63-17843 etc.

For detection of the labeling substance, the detection method can be suitably selected by those skilled in the art, depending on the labeling substance used. For example, when peroxidase is used as the labeling substance, the labeling substance can be detected by adding a substrate for the enzyme, for example a coloration substrate such as tetramethyl benzidine or o-phenylene diamine and aqueous hydrogen peroxide, and then measuring a change in optical density as the degree of coloration of a product by the enzyme reaction. When a fluorochrome or a chemoluminescent substance is used, a method of measuring the fluorescence or emission of a solution after the reaction can be mentioned.

Other constituent ingredients which can be added to the kit 1 of the present invention can be exemplified by detection reagents for the labeling substance, a reagent labeling the "antibody recognizing β2-GPI/oxLDL complex", etc. In addition to these constituent ingredients, a blocking substance, a washing solution, a sample diluent, an enzyme reaction termination solution etc. may be contained.

These constituent ingredients can be accommodated respectively in separate containers and stored as a kit which can, at use, be used according to the measurement method 1 of the present invention.

Measurement of the β2-GPI/oxLDL complex by using the kit 1 of the present invention can be carried out according to the measurement method 1 of the present invention.

The kit 1 of the present invention is used preferably in detection of a disease. The "disease" detected by the kit 1 of the present invention is preferably selected from the group consisting of APS, thrombosis, arterial thrombosis, venous thrombosis, pregnancy morbidity, renal disease, arteriosclerosis (cerebral infarction, myocardial infarction etc.) and diabetes. Detection of the disease by using the kit 1 of the present invention can be carried out according to the detection method 1 of the present invention.

The "sample" used herein is not particularly limited insofar as it is derived from the living body of an animal subjected to detection of a disease, and specifically blood etc. can be mentioned. Other description of the "sample" is the same as described above in the "standard of the present invention".

<5> Antigen of the Present Invention

<5>-1 Antigen 1 of the Present Invention

The antigen 1 of the present invention is an antigen for measuring "antibody recognizing β2-GPI/oxLDL complex" in a sample, which comprises "complex having oxLDL bound covalently to β2-GPI" as an ingredient.

A description of the "complex having oxLDL bound covalently to β2-GPI" as the ingredient in the antigen 1 of the present invention is the same as described above in the "standard 1 of the present invention". The antigen 1 of the present invention, similar to the standard 1 of the present invention, may contain other ingredients insofar as such β2-GPI/oxLDL complex is contained as an ingredient, and a description and examples of the "other ingredients" are the same as described above in the "standard 1 of the present invention".

A description etc. of the form etc. of the antigen 1 of the present invention is the same as described above in the "standard 1 of the present invention". The meaning of the "sample" is also the same as described in the "standard of the present invention".

<5>-2 Antigen 2 of the Present Invention

The antigen 2 of the present invention is an antigen for measuring "antibody recognizing β2-GPI/oxLDL complex" in a sample, which comprises "β2-GPI/oxLDL complex obtainable by incubating oxLDL and β2-GPI under the conditions of 37° C. and pH 7.4 for 16 hours".

A description of the "β2-GPI/oxLDL complex obtainable by incubating oxLDL and β2-GPI under the conditions of 37° C. and pH 7.4 for 16 hours" is the same as described in the "standard 2 of the present invention". Accordingly, the "β2-GPI/oxLDL complex obtainable by incubating oxLDL and β2-GPI under the conditions of 37° C. and pH 7.4 for 16 hours" as the ingredient of the antigen 2 of the present invention preferably has the following properties (a) and (b):

(a) oxLDL and β2-GPI constituting the complex are substantially not dissociated even in the coexistence of 100 U/ml heparin, and (b) oxLDL and β2-GPI constituting the complex are substantially not dissociated even in the coexistence of 10 MM $MgCl_2$.

The method of producing the β2-GPI/oxLDL complex having the properties (a) and (b) is also the same as described above in the "standard 2 of the present invention".

The antigen 2 of the present invention, similar to the standard 1 of the present invention, may contain other ingredients insofar as such β2-GPI/oxLDL complex is contained as an ingredient, and a description and examples of the "other ingredients" are the same as described above in the "standard 1 of the present invention".

A description etc. of the form etc. of the antigen 2 of the present invention is the same as described above in the "standard 1 of the present invention". The meaning of the "sample" is also the same as described in the "standard of the present invention".

The "antibody recognizing β2-GPI/oxLDL complex" as the subject of measurement using the antigen of the present invention includes, but is not limited to, autoantibody, the antibody described in the kit 1 of the present invention, etc.

Any antigen of the present invention binds to the "antibody recognizing β2-GPI/oxLDL complex" and can, by virtue of this property, be used in measurement of the "antibody recognizing β2-GPI/oxLDL complex".

<6> Measurement Method 2 of the Present Invention

The measurement method 2 of the present invention is a method of measuring "antibody recognizing β2-GPI/oxLDL complex" in a sample, which comprises using the antigen of the present invention.

The "antigen of the present invention" used herein may be either antigen 1 or 2 of the present invention. Its description is as described above.

How the measurement method 2 of the present invention is specifically carried out is not limited insofar as the antigen of the present invention is used. Examples of the specific method are the same as in the "measurement method 1 of the present invention" described above. In the measurement method 2 of the present invention, however, the antigen of the present invention is used preferably in a form immobilized on a solid phase. That is, the measurement method 2 of the present invention is preferably a method using the "solid phase of the present invention" described later.

The meaning of the "sample" is the same as described above in the "standard of the present invention". The "antibody recognizing β2-GPI/oxLDL complex" is the same as described above in the "antigen of the present invention".

<7> Detection Method 2 of the Present Invention

The detection method 2 of the present invention is a method of detecting a disease, which comprises measuring "antibody recognizing β2-GPI/oxLDL complex" in a sample by using the measurement method 2 of the present invention and correlating the measured "antibody in the sample" with a disease.

In the detection method 2 of the present invention, the "antibody recognizing β2-GPI/oxLDL complex" in a sample is first measured by the measurement method 2 of the present invention. A description of the measurement method 2 of the present invention is as described above. The "sample" used herein is not particularly limited insofar as it is derived from the living body of an animal subjected to detection of a disease, and specifically blood etc. can be mentioned. Other description of the "sample" is the same as described above in the "standard of the present invention".

In the detection method 2 of the present invention, the "antibody recognizing β2-GPI/oxLDL complex in a sample" measured by using the measurement method 2 of the present invention is then correlated with a disease to detect the disease.

The "measured 'antibody recognizing β2-GPI/oxLDL complex in a sample'" mentioned herein may be measured for its "amount" in the sample (quantitative measurement result) or its "presence or absence" in the sample (qualitative measurement result), similar to the above description of the "detection method 1 of the present invention".

The "amount" may be an observed value or a relative value similar to the above description of the "detection method 1 of the present invention".

The amount of the "antibody recognizing β2-GPI/oxLDL complex" is increased by a certain disease so that when the amount of the antibody in a sample is higher than that of a healthy person, the sample can be correlated with "contraction of the disease" or "high possibility of contraction of the disease". When the amount of the antibody in a sample is equal to that of a healthy person, the sample can be correlated with "absence of contraction of the disease" or "low possibility of contraction of the disease".

The detection method 2 of the present invention, similar to the detection method 1 of the present invention, can be used in detecting not only the contraction of a disease but also the severity of a disease, and the "disease" detected by the detection method 2 of the present invention, similar to the detection method 1 of the present invention, is preferably selected from the group consisting of APS, thrombosis, arterial thrombosis, venous thrombosis, pregnancy morbidity, renal disease, arteriosclerosis (cerebral infarction, myocardial infarction etc.) and diabetes.

<8> Solid Phase of the Present Invention

The solid phase of the present invention is a solid phase having the antigen of the present invention immobilized thereon.

As used herein, the "antigen of the present invention" may be either antigen 1 or 2 of the present invention. Its description is as described above.

The solid phase used in immobilizing the antigen of the present invention is not particularly limited insofar as it is capable of immobilizing the antigen of the present invention, and is insoluble in water, a sample and a measurement reaction solution. The solid phase can be in the form of a plate (e.g. a microplate well etc.), a tube, beads, a membrane, gel etc. The material of the solid phase includes polystyrene, polypropylene, nylon, polyacrylamide etc.

Among these, a plate made of polystyrene is preferable.

As the method of immobilizing the antigen of the present invention onto the solid phase, it is possible to employ a physical adsorption method, a covalent bonding method, and general methods of immobilizing protein or lipid.

Among these methods, the physical adsorption method is preferable because this method is easy in procedure and used frequently.

Specifically, the physical adsorption method includes, for example, a method of adsorbing the antigen of the present invention onto a solid phase (for example a microplate) by dissolving the antigen of the present invention in a buffer solution or the like, and contacting the solution with the solid phase.

In the surface of the solid phase having the antigen of the present invention immobilized thereon, there may remain a surface region not having the antigen thereon, and when the "antibody recognizing β2-GPI/oxLDL complex" and other molecular species in a sample are immobilized on such antigen-free region, accurate measurement results cannot be obtained in some cases. Accordingly, it is preferable that before contacting a sample with the solid phase, a blocking substance is added to the solid phase so that the region not having the antigen immobilized thereon is covered therewith. The blocking substance includes serum albumin, casein, skim milk and gelatin, and products commercially available as the blocking substance can also be used.

Specifically, the blocking method includes, for example, a method that involves adding e.g. a blocking substance (serum albumin, casein, skim milk, gelatin etc.) to the solid phase and storing it at about 37° C. for 30 minutes to 2 hours or at ordinary temperatures (15 to 25° C.) for 1 to 2 hours.

<9> Kit 2 of the Present Invention

The kit 2 of the present invention is a kit for measurement of "antibody recognizing β2-GPI/oxLDL complex" in a sample, which comprises the solid phase of the present invention as a constituent ingredient.

The kit 2 of the present invention may contain other constituent ingredients insofar as it contains the solid phase of the present invention as a constituent ingredient. It is particularly preferable that the kit 2 further contains, as a constituent ingredient, a substance binding to the "antibody recognizing 'β2-GPI/oxLDL complex'".

Although the "substance binding to the 'antibody recognizing β2-GPI/oxLDL complex'" is not particularly limited insofar as it binds to the "antibody recognizing β2-GPI/oxLDL complex", the "substance" is for example an antibody which depending on the animal, class etc. from which the "antibody recognizing β2-GPI/oxLDL complex'" (immunoglobulin) was derived, binds specifically to the immunoglobulin. For example, when the "antibody recognizing β2-GPI/oxLDL complex" is mouse-derived IgG1, an anti-mouse IgG1 antibody can be used as the "substance binding to the 'antibody recognizing β2-GPI/oxLDL complex'".

The "substance binding to 'antibody recognizing β2-GPI/oxLDL complex'" is preferably labeled with a labeling substance to make detection easy.

Instead of labeling the "substance binding to 'antibody recognizing β2-GPI/oxLDL complex'" itself, a substance binding to the "substance binding to 'antibody recognizing β2-GPI/oxLDL complex'" may be labeled.

A description of the labeling substance used in such labeling, and a description of the detection of the labeling substance, are the same as described above in the "kit 1 of the present invention".

Other constituent ingredients which can be added to the kit 2 of the present invention can be exemplified by detection reagents for the labeling substance, a reagent labeling the "substance binding to 'antibody recognizing β2-GPI/oxLDL complex'", etc. In addition to these constituent ingredients, a blocking substance, a washing solution, a sample diluent, an enzyme reaction termination solution etc. may be contained.

These constituent ingredients can be accommodated respectively in separate containers and stored as a kit which can, at use, be used according to the measurement method 2 of the present invention.

Measurement of the "antibody recognizing β2-GPI/oxLDL complex" by using the kit 2 of the present invention can be carried out according to the measurement method 2 of the present invention.

The kit 2 of the present invention is used preferably in detection of a disease. The "disease" detected by the kit 2 of the present invention, similar to the "kit 1 of the present invention" described above, is preferably selected from the group consisting of APS, thrombosis, arterial thrombosis, venous thrombosis, pregnancy morbidity, renal disease, arteriosclerosis (cerebral infarction, myocardial infarction etc.) and diabetes.

Detection of the disease by using the kit 2 of the present invention can be carried out according to the detection method 2 of the present invention.

The "sample" used herein is not particularly limited insofar as it is derived from the living body of an animal subjected to detection of a disease, and specifically blood etc. can be mentioned. Other description of the "sample" is the same as described above in the "standard of the present invention".

<10> Measurement Method 3 of the Present Invention

The measurement method 3 of the present invention is a method of measuring an immune complex in a sample, which comprises using "antibody recognizing β2-GPI" and/or "antibody recognizing LDL" and an anti-IgG antibody.

According to the measurement method 3 of the present invention, an IgG immune complex formed with β2-GPI or LDL can be detected.

The "antibody recognizing β2-GPI" is not particularly limited, but is preferably Cof-23. The "antibody recognizing LDL" is not particularly limited either, but is preferably anti-apoB100 antibody (1D2). The "anti-IgG antibody" is not particularly limited either, and can be exemplified by an antibody which depending on the animal, class etc. from which the IgG (immunoglobulin G) constituting the immune complex was derived, binds specifically to the IgG. For example, when the IgG constituting the immune complex is derived from humans, an anti-human IgG antibody can be used as the anti-IgG antibody.

These antibodies are preferably those immobilized on a solid phase. The solid phase which can be used herein is the same as the "solid phase of the present invention" described above. The meaning of the "sample" is the same as described in the "standard of the present invention".

Hereinafter, the present invention will be described in more detail by reference to the Examples, but the present invention is not limited thereto. Number in brackets in the Examples refers to reference number in the list of references shown later.

First, materials, methods etc. used in the Examples will be described.

(1) Monoclonal Antibody

Cof-22 (IgG1, κ) and Cof-23 (IgG1, κ): Anti-human β2-GPI antibodies which are established from BALB/c mice immunized with human β2-GPI [reference 2], both of which bind in solution to monomeric β2-GPI.

WB-CAL-1 (IgG2a, κ): Anti-β2-GPI autoantibody which is an antibody derived from WB F1 mice [reference 8].

EY2C9 (IgM): Anti-β2-GPI autoantibody which is an antibody established from peripheral-blood lymphocytes in patients with APS [reference 9].

WB-CAL-1 and EY2C9 both bind to only "β2-GPI having formed a complex with negatively charged PLs" or "2-GPI having formed a complex with oxLDL" and do not bind in solution to monomeric β2-GPI.

1D2 (IgG): Mouse monoclonal anti-human apoB100 antibody binding to both oxLDL and native LDL and obtained from YAMASA CORPORATION.

(2) Preparation of Human β2-GPI

According to a method described in [reference 10], β2-GPI was purified from plasma in healthy persons. The pooled plasma from healthy persons was purified by a heparin-Sepharose column, a DEAE-cellulose column and an anti-β2-GPI affinity column. For preventing contamination of β2-GPI with various immunoglobulins G, fractions rich in β2-GPI were further passed through a protein A-Sepharose column. The final β2-GPI fraction was delipidated by sufficient washing with n-butanol.

(3) Isolation and Oxidization of LDL

According to a method described in [reference 11], LDL (d=1.019 to 1.063 g/ml) was isolated by ultracentrifuging fresh plasma from healthy persons. The isolated LDL was adjusted to 100 μg/ml and oxidized by incubation for varying times at 37° C. together with 5 μM CuSO$_4$ (10 mM Hepes, 150 mM NaCl, pH 7.4 (Hepes buffer)). The oxidization was terminated by adding EDTA (final concentration 1 mM), and this LDL was dialyzed against Hepes buffer containing 1 mM EDTA. The degree of oxidation was evaluated by a thiobarbituric acid reactive substance (TBARS) value [reference 12].

(4) Synthesis of an Oxysterol Derivative of 9-Carboxynonanoate

7-Ketocholesteryl-9-carboxynonanoate (oxLig-1) was synthesized according to a method described in [reference 7]. 22-Ketocholesteryl-9-carboxynonanoate (9-COOH-22KC) was also synthesized in an analogous manner. That is, 19.2 mg (0.10 mmol) 1-ethyl-3-(3-dimethylaminopropyl)carbodiimide hydrochloride and 6.1 mg (0.80 mmol) 4-(dimethylamino)pyridine were added to a solution of 10 mg (0.025 mmol) 22-ketocholesterol and 14.1 mg (0.075 mmol) azelaic acid in acetone (1 ml). The mixture was stirred at room temperature for 2 days, concentrated and extracted with chloroform. The extract was washed successively with 2 M hydrochloric acid, dried over magnesium sulfate anhydride and evaporated. The residues were applied to chromatography on a silica gel column with toluene/ethyl acetate (3/1, v/v) to give 9-COOH-22KC (8.5 mg, yield 61%). The analysis result by $^1$H NMR is as follows:

$^1$H-NMR (300 MHz, CDCl$_3$) δ=5.35 (d, $^1$H, J 5.1 Hz, H-6), 4.59 (m, $^1$H, H-3)

In the $^1$H NMR spectrum of 9-COOH-22KC similar to oxLig-1, a signal of H-3 was detected as multiplet at a position of δ=4.59 ppm. This result indicated that the hydroxyl group at this position had been esterified. Although the spectrum showed a signal of olefin proton H-6 in a lower magnetic field, the spin-spin coupling thereof with its adjacent methylene group was observed. The molecular weight of 9-COOH-22KC was identical with that of oxLig-1. 9-COOH-22KC was positive in the Lieberman-Burchard reaction, and revealed the absence of bound ketone at 7-position.

(5) Ligand Blotting Analysis on a Thin-Layer Chromatography (TLC) Plate

For conducting TLC ligand blotting, the lipid was spotted on a Polygram silica gel G plate (manufactured by Machery-Nagel) and developed with chloroform/methanol (8/1, v/v). The ligand blotting analysis was conducted according to a method described in [reference 7]. That is, the plate was dried and blocked with PBS containing 1% bovine serum albumin (BSA), and then the plate was incubated for 1 hour together with the β2-GPI and anti-β2-GPI antibodies (Cof-22 and EY2C9). Then, the plate was incubated for 1 hour with horseradish peroxidase (HRP)-labeled anti-mouse IgG antibody or anti-human IgM antibody. Between each step, the plate was washed sufficiently with PBS. Coloration was conducted using H$_2$O$_2$ and 4-methoxy-1-naphthol. In a TLC plate of control, the separated ligand was stained with I$_2$ vapor.

(6) ELISA for Detection of β2-GPI/oxLDL Complex

8 μg/ml anti-β2-GPI antibody (WB-CAL-1) solution in Hepes buffer was put in a volume 50 μl/well to a microtiter plate (Immulon 2HB, Dynex Technologies Inc.) and adsorbed onto each well by incubating the plate overnight at 4° C. This plate was blocked with 1% skim milk for 1 hour. A serum sample (100-fold dilution) or a solution containing β2-GPI/oxLDL complex or oxLDL was added to each well (100 μl/well) and incubated for 2 hours. In some experiments, exogenous β2-GPI was allowed to be present (25 μg/ml) in this step. Then, each well was incubated for 1 hour together with biotin-labeled anti-apoB100 antibody (1D2), and was incubated for 30 minutes with HRP-labeled avidin. Coloration was conducted using o-phenylene diamine and H$_2$O$_2$. The coloration reaction was terminated by adding 2 N sulfuric acid, and OD at 490 nm was measured. Among these steps, each well was washed sufficiently with Hepes buffer containing 0.05% Tween 20. The optical density (OD) of each sample in the assay was corrected by the average OD of the blank wells. 1.0 U/ml was adjusted to be 3 times as high as the standard deviation of the mean of serum samples from 50 healthy persons, and as a result, 1.0 U/ml oxLDL12h/β2-GPI16h complex corresponded to about 4.5 μg/ml in terms of apoB. Samples having reactivity higher than 1.0 U/ml were expressed as positive.

(7) ELISA for Detection of Anti-β2-GPI/Lipid IgG Antibody

CL (derived from bovine heart, manufactured by Sigma), oxLig-1 or 9-COOH-22KC (50 μg/ml ethanol, 50 μl/well) was adsorbed by evaporation onto a polystyrene plate (Immulon 1B; Dynex Technologies Inc.), and this plate was blocked with 1% BSA. In each well, the purified monoclonal autoantibody or serum sample (100-fold dilution) was incubated for 1 hour in the presence or absence of β2-GPI (25 μg/ml), and then HRP-labeled anti-mouse IgG or anti-human IgG or IgM was added to each well.

The subsequent step was carried out according to the method described in the "ELISA for detection of β2-GPI/oxLDL complex". The optical density (OD) of each sample was corrected by the average OD of the blank wells, and its antibody titer was calculated by using the positive standard in the living body. When the antibody titer in a sample was more than 3 times as high as the standard deviation of the mean of plasma samples from 50 healthy persons, the sample was expressed as positive.

(8) ELISA for Detection of Anti-β2-GPI IgG Antibody

ELISA for detection of anti-β2-GPI IgG antibody was carried out by a method described in [reference 1]. That is, β2-GPI was put in a volume of 10 μg/ml (50 μl/well) to a polyoxidized polystyrene plate (carboxylated, Sumilon C, Sumitomo Bakelite Co., Ltd.) and adsorbed onto each well by overnight incubation at 4° C., and this plate was blocked with 3% gelatin. A serum sample was diluted 100-fold and incubated for 1 hour in each well. Then, HRP-labeled anti-human IgG was added to the plate. The subsequent step was carried out according to the method described in the "ELISA for detection of β2-GPI/oxLDL complex".

(9) ELISA for Detection of IgG Immune Complex

For detection of IgG immune complex formed with β2-GPI or LDL, the anti-β2-GPI antibody (Cof-23) or anti-apoB100 antibody (1D2) was put in an amount of 5 μg/ml (50 μl/well) to a polystyrene plate (Immulon 1B) and adsorbed onto each well by overnight incubation at 4° C. Then, this plate was blocked with 1% BSA. A serum sample (100-fold dilution) was incubated for 1 hour in each well, and then HRP-labeled anti-human IgG was added thereto. The subsequent step was carried out according to the method described in the "ELISA for detection of β2-GPI/oxLDL complex".

(10) ELISA for Detection of the "Antibody Recognizing β2-GPI/oxLDL Complex"

The oxLDL12h/β2-GPI16h complex (10 μg/ml, 50 μg/well) was incubated at 4° C. overnight in each well in a polystyrene plate (Immulon 1B) and blocked with PBS containing 1% BSA. Then, a serum sample diluted 100-fold with PBS containing 0.3% BSA was put to each well, reacted for 1 hour and then reacted for 1 hour with HRP-labeled anti-human IgG. The well was colored in a usual manner by adding o-phenylene diamine and $H_2O_2$, the reaction was terminated with sulfuric acid, and the absorbance at 490 nm was measured.

(11) Statistical Analysis

Statistical analysis was carried out by using StatView Software (Abacus Concepts). In the case of comparing autoantibody with clinical profile, the Fisher's extract test was used. The confidence interval (C.I.) at the 95% confidence level was calculated by the Woolf method.

(12) Serum Sample

The patients from whom the serum samples used in the Examples were derived are constituted as shown in Table 1.

TABLE 1

|  | No | % |
|---|---|---|
| Patients |  |  |
| SLE only | 44 |  |
| APS | 83 |  |
| Primary | 46 | 55.4 |
| Complication with SLE | 37 | 44.6 |
| Clinical profile |  |  |
| Thrombosis | 71 | 55.9 |
| Arterial thrombosis only | 26 | 20.5 |
| Venous thrombosis only | 27 | 21.3 |
| Arterial or venous thrombosis | 18 | 14.2 |
| Pregnancy morbidity | 31/116 | 26.7 |
| Thrombocytopenia | 23/123 | 18.7 |
| Autoantibodies |  |  |
| β2-GPI-dependent IgG aCL (anti-β2-GPI/CL IgG antibody) | 73/127 | 57.5 |
| Anti-β2-GPI IgG antibody | 46/127 | 36.2 |
| Anti-β2-GPI/oxLig-1 IgG antibody | 60/127 | 47.2 |
| Lupus anticoagulants | 59/108 | 54.6 |
| β2-GPI/oxLDL complex | 72/127 | 56.7 |

Results (1) Role of 7-Ketone as a β2-GPI-Binding Ligand

For comparing two ω-carboxyl oxysterol esters mutants different in ketone position (that is, 7-ketocholesteryl-9-carboxynonanoate [oxLig-1] and 22-ketocholesteryl-9-carboxynonanoate [9-COOH-22KC]) for their binding to β2-GPI, they were subjected to ligand blotting and to ELISA using anti-β2-GPI antibody as a probe. In the ligand blotting for detection by Cof-22 antibody and EY2C9 antibody, β2-GPI bound predominantly to the 7-keto mutant (oxLig-1) but not to 9-COOH-22KC (FIG. 1). As a result of detection by the anti-β2-GPI antibody (Cof-22, WB-CAL-1 or EY2C9) in ELISA using a plate coated with the ligand, β2-GPI bound more strongly to immobilized oxLig-1 than to immobilized 9-COOH-22KC (Table 2). These data reveal that the ketone at 7-position in the cholesterol skeleton is a determinative group essential for interaction of high affinity between β2-GPI and its ligand "$Cu^{2+}$-oxLDL-derived oxLig-1".

TABLE 2

| Immobilized lipid | β2-GPI-binding(OD) | | |
|---|---|---|---|
|  | w/Cof-22 | w/WB-CAL-1 | w/EY2C9 |
| oxLig-1 | 1.194 +/− 0.099 (0.041 +/− 0.001) | 0.441 +/− 0.007 (0.013 +/− 0.004) | 0.878 +/− 0.031 (0.013 +/− 0.001) |
| 9-COOH-22KC | 0.217 +/− 0.016 (0.067 +/− 0.013) | 0.063 +/− 0.004 (0.031 +/− 0.011) | 0.130 +/− 0.024 (0.046 +/− 0.008) |

Figure 2:
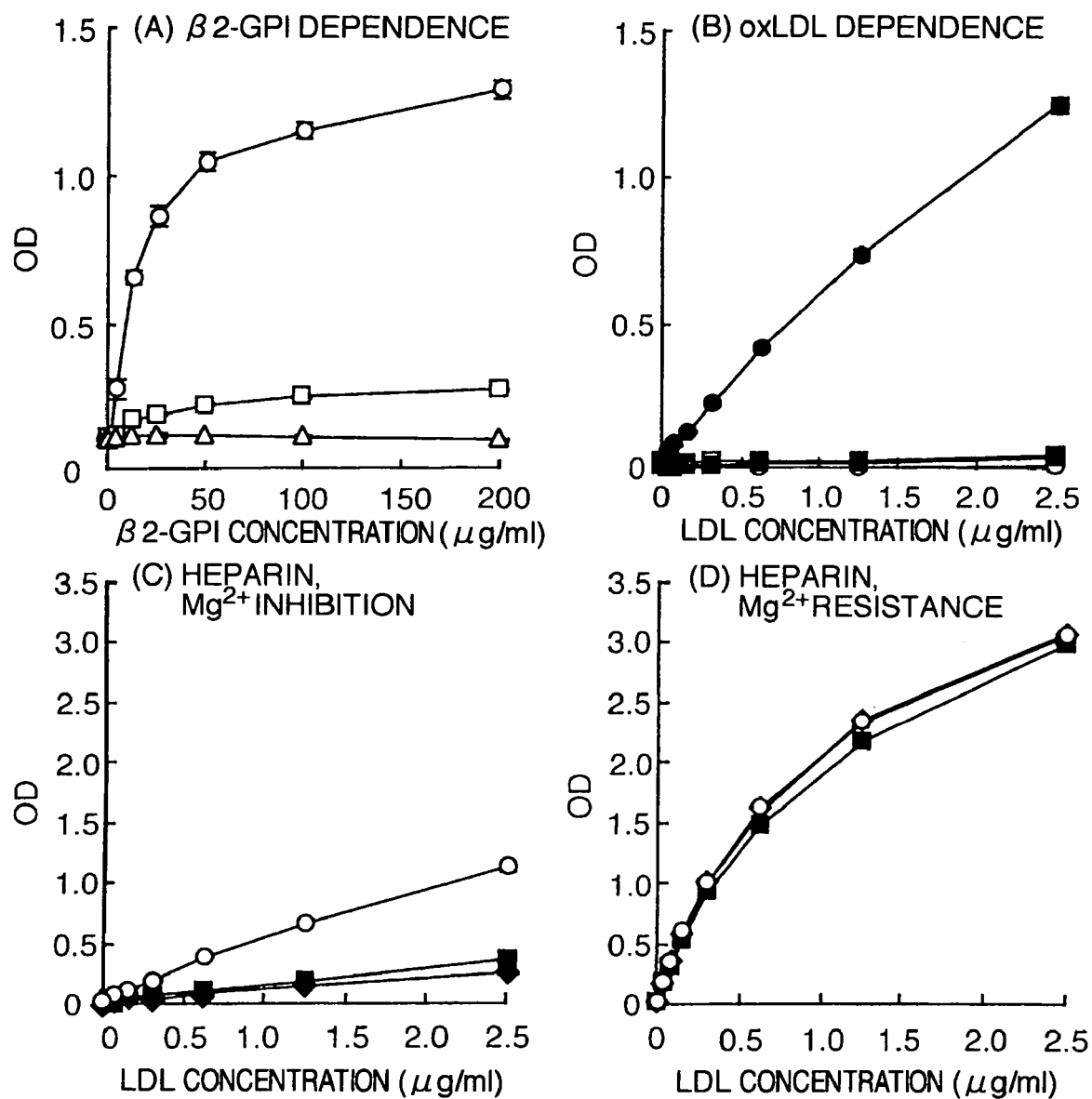
FIG. 2 is a graph showing a profile of formation of Cu$^{2+}$-oxidized oxLDL/β2-GPI complex.
(A) ELISA for detecting β2-GPI/oxLDL complex was conducted by incubating oxLDL12h (0 μg/ml (white triangle), 0.16 μg/ml (white square) or 2.5 μg/ml (white circle), in terms of apoB) together with β2-GPI at various concentrations in wells.
(B) ELISA was conducted by incubating oxLDL12h (LDL treated with 5 μM CuSO$_4$ at 37° C. for 12 hours; circle) or native LDL (square) at the concentrations shown in the graph in the absence (white) or presence (25 μg/ml; black) of β2-GPI.
(C) ELISA was conducted by incubating oxLDL12h at the concentrations shown in the graph and β2-GPI (25 μg/ml) in the absence (white circle) or presence (black square) of heparin (100 U/ml) or in the presence (black lozenge) of MgCl$_2$ (10 mM) in wells.
(D) The oxLDL12h/β2-GPI16h complex was prepared by incubating oxLDL12h (100 μg/ml) at 37° C. for 16 hours together with β2-GPI (100 μg/ml). Using this complex (2.5 μg/ml in terms of apoB), ELISA was conducted in the absence (white circle) or presence (black square) of heparin (100 U/ml) or in the presence (black lozenge) of MgCl$_2$ (10 mM). The data are shown by the mean±SD of 3 samples.

LDL (100 μg/ml) was oxidized by incubation with 5 μM $CuSO_4$ at 37° C. for 12 hours (oxLDL thus obtained is referred to as "oxLDL12h") and the oxidation was terminated by adding EDTA. As a result of ELISA for detection of β2-GPI/oxLDL complex, the OD was increased only when oxLDL12h was incubated with exogenous β2-GPI in a well. Formation of the complex depended on the concentrations of both β2-GPI and oxLDL (FIG. 2A, B). Significant formation of the complex occurred only when oxLDL12h was used, but did not occur when native LDL was used. Formation of the complex at pH 7.4 was cancelled almost completely in the presence of heparin or $MgCl_2$ (FIG. 2C). This inhibition was also observed similarly in the presence of $CaCl_2$ (data are not shown). From these data, it was revealed that β2-GPI can form an initially dissociable non-covalent complex with oxLDL12h. On the other hand, when oxLDL12h was incubated with β2-GPI at pH 7.4, 37° C. for 16 hours, a relatively stable oxLDL/β2-GPI complex was consistently observed (oxLDL12h/β2-GPI16h). Even if heparin or $MgCl_2$ was added at pH 7.4, formation of the oxLDL12h/β2-GPI16h complex could not be disintegrated (FIG. 2D).

Figure 3:
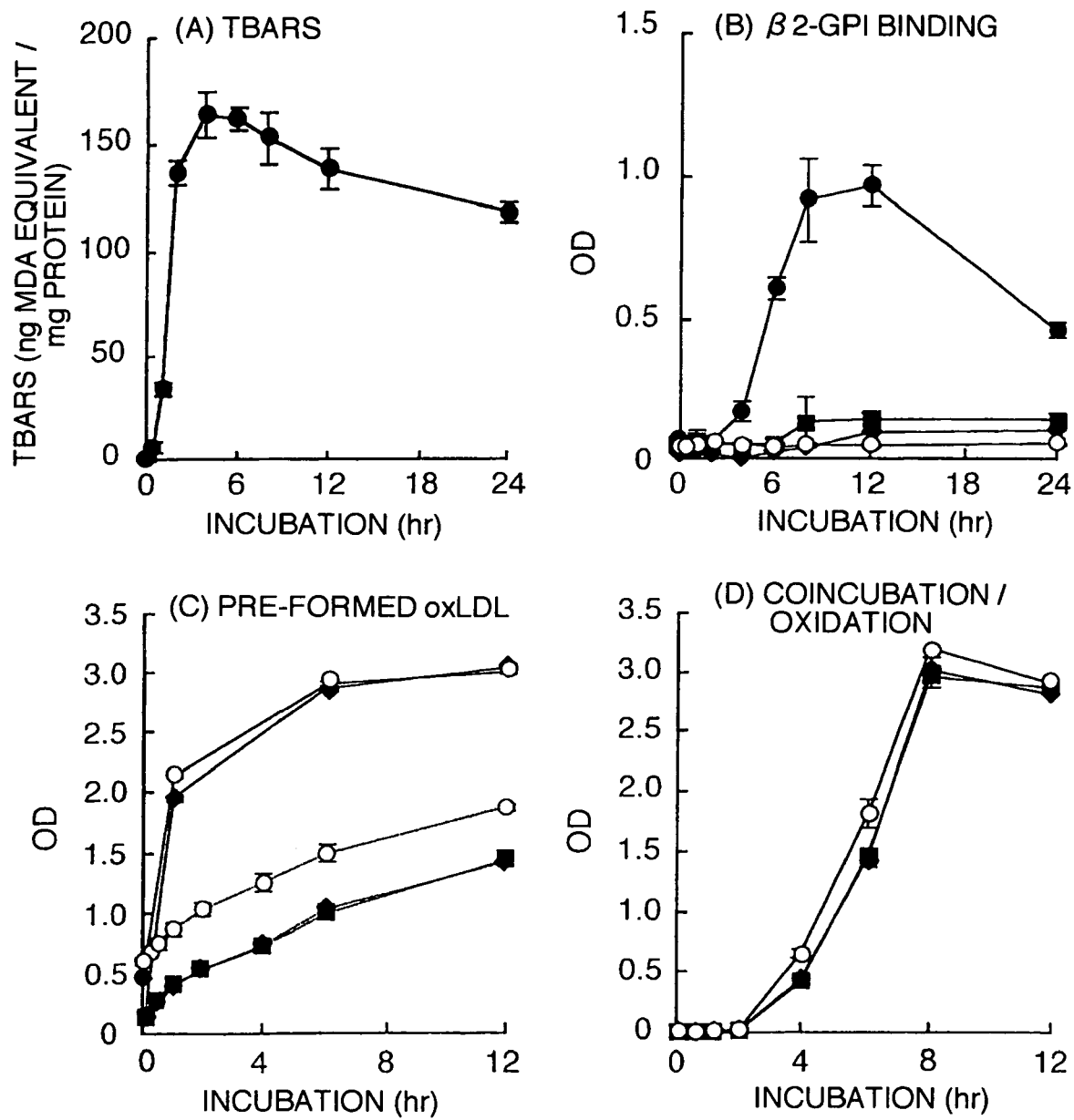
FIG. 3 is a graph showing a change with time of formation of Cu$^{2+}$-oxidized oxLDL/β2-GPI complex.

For further examination of this process, various experiments with time were conducted. FIG. 3A is a graph showing time-dependent formation of TBARS in LDL treated with $CuSO_4$. The LDL preparation exposed to $Cu^{2+}$ ion at 37° C. formed TBARS rapidly, and its peak was detected after 4 hours. On the other hand, LDL oxidation causing binding to β2-GPI proceeded with a slight delay, and reached the maximum level after about 12 hours (FIG. 3B) This complex formation was inhibited almost completely by addition of heparin or $MgCl_2$. These data agreed with the previous finding [reference 6] that β2-GPI binds to $Cu^{2+}$-oxLDL, but not to "LDL modified with MDA".

Previously formed oxLDL12h was incubated with β2-GPI for varying times under the condition of 4° C. or 37° C. (their final concentrations were 100 μg/ml and 100 μg/ml respectively) (FIG. 3C). Formation of the β2-GPI/oxLDL complex depended on temperature and time. This complex was not dissociated even by incubation under the condition of pH 7.4 in the presence of heparin or $MgCl_2$. FIG. 3D is a graph showing that during the process of oxidation with $Cu^{2+}$, stable interaction between β2-GPI and oxLDL is formed even in the presence of β2-GPI.

(3) Stability of β2-GPI/oxLDL Complex In Vitro at Various pH Values

At neutral pH, there appeared the stable complex which is considered as a Schiff base adduct formed between a lysine residue, ε-amine of β2-GPI and aldehyde formed oxidatively via Cu2+ on oxLDL. For confirming this, the stability of the complex not reduced or reduced with $NaCNBH_3$ was analyzed under basic pH condition. As shown in FIG. 4, the dissociation of reduced oxLDL12h/β2-GPI16h complex was not observed in the absence of $MgCl_2$ under the pH condition used in this examination. In the presence of $MgCl_2$, 82% of the non-reduced complex was dissociated and 69% of the reduced complex was dissociated at pH 10. This phenomenon indicated that the adduct is not a Schiff base, or that even if the adduct is a Schiff base, the adduct is in an environment where it cannot contact with $NaCNBH_3$ (e.g., a hydrophobic pocket).

(4) Indissociable β2-GPI/oxLDL Complex in Serum from Patients

Serum samples from patients with APS and/or SLE were screened to examine whether or not the β2-GPI/oxLDL complex occurred at high level. First, the β2-GPI/oxLDL complex was identified in 20 serum samples. This group showed the serum complex at high concentrations of 2.1 to 13.7 U/ml (average concentration: 4.48 U/ml (cut-off value: 1.0 U/ml)). As shown in FIG. 5, native LDL even upon incubation at 37° C. for 16 hours together with β2-GPI did not form the complex. On the other hand, the oxLDL12h/β2-GPI16h complex is stable under the condition of pH 7.4, even in the presence of heparin or $MgCl_2$. Even in the oxLDL/β2-GPI complex detected in 5 serum samples at pH 7.4, a typical binding pattern was observed. In all the 20 samples, the complex formed in vivo was stable at neutral pH, even in the presence of heparin or $MgCl_2$ (ODs in the presence of heparin and $MgCl_2$ were 121±25.1% and 128±13.6%, respectively, based on that under the control conditions). The complex formed in the pre-stage, present in the serum samples, was observed consistently (104±10.9%) even after incubation with $MgCl_2$ at pH 10, 37° C. for 16 hours (under this condition, the complex formed in vitro could be dissociated) (FIG. 4). From these findings, it is considered that the indissociable, covalent adduct is formed in vivo between β2-GPI and oxLDL. The in vitro adduct observed in this experiment is considered as an intermediate product in formation of the indissociable complex.

(5) Clinical Significance of β2-GPI/oxLDL Complex and its Autoantibody

An apparent calibration curve of oxLDL12h/β2-GPI16h complex in the range of 10 ng/ml to 1.25 μg/ml in terms of apoB was prepared in ELISA. Because the WB-CAL-1 antibody used had high specificity for 2-GPI having formed the complex with oxLDL, this ELISA was not influenced by endogenous and monomeric 2-GPI present at high concentration in the serum sample. In this experiment, the β2-GPI/oxLDL complex was observed in 58.7% (27/46) of patients with primary APS, 54.1% (20/37) of patients with APS accompanied by SLE (secondary APS), and 56.8% (25/44) of patients with SLE not accompanied by APS (FIG. 6). This complex was also positive in 18.6% (16/86) of patients with chronic nephritis (diagnosed by renal biopsy).

Anti-β2-GPI/oxLig-1 IgG antibody was observed in 71.7% (33/46) of the patients with primary APS, 59.5% (22/37) of the patients with APS accompanied by SLE (secondary APS), and 11.4% (5/44) of the patients with SLE not accompanied by APS.

The antibody titer of anti-β2-GPI/oxLig-1 IgG antibody in this group of 127 patients was strongly correlated with the antibody titers of both β2-GPI-dependent IgG aCL and anti-β2-GPI IgG antibody (whose correlation coefficients $r^2$ are 0.69 and 0.81 respectively) (FIG. 7). As shown in FIG. 8, there was good correlation between "anti-β2-GPI IgG antibody" and "β2-GPI-containing IgG immune complex" ($r^2=0.50$) (FIG. 8A); "anti-β2-GPI/oxLig-1 IgG antibody" and "β2-GPI-containing IgG immune complex" ($r^2=0.50$) (FIG. 8B); and "β2-GPI-containing IgG immune complex" and "LDL-containing IgG immune complex" ($r^2=0.40$) (FIG. 8C). However, good correlation was not observed between the level of β2-GPI/oxLDL complex and the antibody titer of these antibodies (data are not shown).

The anti-β2-GPI/oxLig-1 IgG antibody in these patients (127 patients with APS and/or SLE) was observed to have significant relationship with history of thrombosis (arterial and/or venous thrombosis, arterial thrombosis and venous thrombosis) and pregnancy morbidity, but not with thrombocytopenia (Table 3). The assay p value (expectation value), odds ratio, and 95% CI in arterial thrombosis were better than those in venous thrombosis, pregnancy morbidity and thrombocytopenia. All the patients were divided into β2-GPI/oxLDL complex positive and negative groups, and the β2-GPI/oxLig-1 IgG antibody was statistically analyzed. As a result, strong correlation between the anti-β2-GPI/oxLig-1 IgG antibody and thrombosis, arterial thrombosis, venous thrombosis and pregnancy morbidity was observed in the β2-GPI/oxLDL complex positive group. The highest correlation was observed with respect to arterial thrombosis.

TABLE 3

| Subjects | Fischer's exact test (p) | Odds ratio | 95% CI |
|---|---|---|---|
| (A) Patients with thrombosis (arterial thrombosis and/or venous thrombosis) (n = 127 in total) | $1.7 \times 10^{-7}$ | 7.65 | 3.41-17.2 |
| (β2-GPI/oxLDL positive, n = 72) | $5.9 \times 10^{-5}$ | 8.21 | 2.79-24.2 |
| (β2-GPI/oxLDL negative, n = 55) | 0.0014 | 6.87 | 2.01-23.5 |
| (B) Patients with arterial thrombosis (n = 127 in total) | $6.9 \times 10^{-7}$ | 7.45 | 3.21-17.3 |
| (β2-GPI/oxLDL positive, n = 72) | $4.8 \times 10^{-5}$ | 10.2 | 2.98-34.7 |
| (β2-GPI/oxLDL negative, n = 55) | 0.0043 | 5.63 | 1.68-18.9 |
| (C) Patients with venous thrombosis (n = 127 in total) | 0.026 | 2.23 | 1.06-4.68 |
| (β2-GPI/oxLDL positive, n = 72) | 0.066 | 2.37 | 0.89-6.29 |
| (β2-GPI/oxLDL negative, n = 55) | 0.20 | 1.93 | 0.61-6.14 |
| (D) Patients with pregnancy morbidity (n = 116 in total) | 0.0052 | 3.31 | 1.39-7.90 |
| (β2-GPI/oxLDL positive, n = 69) | 0.014 | 4.43 | 1.27-15.4 |
| (β2-GPI/oxLDL negative, n = 47) | 0.12 | 2.67 | 0.74-9.61 |
| (E) Patients with thrombocytopenia (n = 123 in total) | 0.25 | 1.53 | 0.61-3.80 |
| (β2-GPI/oxLDL positive, n = 70) | 0.22 | 1.93 | 0.58-6.50 |
| (β2-GPI/oxLDL negative, n = 53) | 0.61 | 1.05 | 0.25-4.46 |

(A) Patients with thrombosis (arterial thrombosis and/or venous thrombosis) (n = 127 in total) (β2-GPI/oxLDL positive, n = 72) (β2-GPI/oxLDL negative, n = 55)
(B) Patients with arterial thrombosis (n = 127 in total)
(C) Patients with venous thrombosis (n = 127 in total)
(D) Patients with pregnancy morbidity (n = 116 in total)
(E) Patients with thrombocytopenia (n = 123 in total)

(6) Detection of "Antibody Recognizing β2-GPI/oxLDL Complex"

The "antibody recognizing β2-GPI/oxLDL complex" in serum was detected by ELISA. Further, the relationship between the "antibody recognizing β2-GPI/oxLDL complex" and the "anti-β2-GPI IgG antibody" was examined. The results are shown in FIG. 9.

Discussion

The present inventors reported that a major lipid ligand involved in binding β2-GPI to oxLDL formed by $Cu^{2+}$ is ω-carboxylated 7-ketocholesterol ester such as 7-ketocholesteryl-9-carboxynonanoate (oxLig-1), and the ω-carboxyl group is essential for recognition of β2-GPI [reference 7]. The interaction between β2-GPI and $Cu^{2+}$-oxLDL in vitro is reversible in an initial stage by treatment with $Mg^{2+}$, but is gradually developed into more stable interaction, requiring $Mg^{2+}$ and high pH for dissociation. On the other hand, a stable and indissociable oxLDL/β2-GPI complex was found in serum samples from patients with APS and/or SLE. Further, an IgG immune complex containing LDL and β2-GPI was detected in these patient serums, and further it was suggested that the β2-GPI/oxLDL complex in serum was correlated with arterial thrombosis.

Formation of foam cells is regarded as a characteristic of the initial development of atheroma, and LDL is a major lipid source accumulated in the foam cells. The binding of modified LDL to a scavenger receptor of macrophage leads to unregulated accumulation of cholesterol, thus leading to foam-cell formation accompanied by atherosclerotic damage. By the present inventor, two major ligand structures giving the binding of β2-GPI to $Cu^{2+}$-oxLDL and anti-β2-GPI antibody-mediated phagocytosis by macrophages respectively were recently identified as 7-ketocholesteryl-9-carboxynonanoate (oxLig-1) and 7-ketocholesteryl-12-carboxy(keto)dodecanoate (oxLig-2) [reference 7].

In this study, bound ketone in 7-position in the cholesterol skeleton of the ligand is essential for high-affinity binding to β2-GPI, and ketone in 22-position cannot be substituted therefor [FIG. 1 and Table 2].

It is reported that a patch consisting of positively charged 14 amino acid residues, and a movable loop, in domain V of β2-GPI are important for interaction with amphiphilic compounds such as CL, phosphatidylserine, phosphatidic acid and phosphatidyl glycerol [references 3 to 5]. It is further reported that this binding region of β2-GPI is also related to interaction with oxLDL [reference 13]. It is estimated that the bound ketone in the ligand, together with the ω-carboxyl group, is orientated towards a hydrophilic space and binds specifically to β2-GPI. Generally, the activity of the bound ketone to form a Schiff base adduct is lower than that of ω-aldehyde. The interaction between oxLDL and β2-GPI is inhibited by any one of $MgCl_2$, $CaCl_2$ and heparin, and it is thus considered that the β2-GPI ligand is involved in non-covalent electrostatic interaction between oxLDL and β2-GPI under neutral pH condition.

At present, it is well-known that in ELISA using a microtiter plate coated with PL, anti-β2-GPI antibody found in serum from patients with APS binds to complexes of β2-GPI and negative charged PLs such as CL, phosphatidylserine and phosphatidic acid [reference 10]. It was also recently revealed that aCL present in patients with APS reacts with a Schiff base adduct formed between oxidized CL and β2-GPI. However, the negatively charged PLs are very minor components of LDL. Products oxidized via $Cu^{2+}$ in LDL include cholesterol and/or oxysterol esterified with 9- or 13-hydroperoxy (or hydroxy)-octadecadienoate, 9-oxononanoate or 9-carboxynonanoate, and some of these products are also present in arteriosclerotic plaques [references 14-16]. As already reported [reference 7], not only oxidized PLs but ωcarboxyl-oxysteryl esters such as oxLig-1 and oxLig-2 were detected as major β2-GPI ligands in $Cu^{2+}$-oxLDL. Characteristics of in vitro and in vivo adducts are not revealed. However, it is highly possible that such compounds are conjugates of β2-GPI and some cholesteryl esters modified by oxidation. In this study, treatment of oxLDL12h/β2-GPI16h complex with an excess (200 mM) of $NaCNBH_3$ was not effective in reduction of imine in the Schiff base adduct. This result revealed a possibility that the stable and indissociable oxLDL/β2-GPI complex is formed by Michael reaction or by other mechanism such as direct oxidation of lysine residues by alkoxyl radicals of polyunsaturated fatty acid.

This study revealed that in patients (54.1 to 58.7%) with APS and/or SLE, oxLDL is circulated as a stable and indissociable complex with β2-GPI. It is reported that oxLDL is incorporated predominantly via a scavenger receptor into macrophages, and leads often to formation of foam cells and atherosclerotic damage. However, there is incomplete formation of oxLDL circulating in blood in patients with arteriosclerosis. In this experiment, free oxLDL in serum from the patient is not measured, but oxLDL formed in vivo is considered to form a complex with endogenous β2-GPI (concentration of β2-GPI in plasma is about 200 µg/ml). As shown in FIG. 3D, LDL having undergone oxidation in vitro forms a stable adduct in the presence of β2-GPI under neutral pH condition as the incubation time is increased. Further, the stable interaction between β2-GPI and oxLDL is observed under various in vitro conditions such as in a buffer solution only, a buffer solution containing 1% BSA, and 50% human serum (data are not shown). Thus, the β2-GPI ligand correlated with oxLig-1 and oxLig-2 causes specific interaction between β2-GPI and oxLDL in the presence of an excess of various plasma/serum proteins, to form a stable complex.

The relationship of aPL with severe clinical complications such as arterial/venous thrombosis, pregnancy morbidity and thrombocytopenia is established in patients with APS. aCL was initially considered to bind to acidic PLs such as CL, but at present, it is widely admitted that β2-GPI is a true antigen for aCL. It was shown in 1998 that anti-β2-GPI IgG antibody can serve as a serum marker of arterial thrombosis for patients with SLE, and also that anti-MDA-LDL IgG antibody is not correlated with arterial thrombosis. This study revealed good relationship among the antibody titers of anti-β2-GPI/CL IgG antibody, anti-β2-GPI IgG antibody, and anti-β2-GPI/oxLig-1 IgG antibody (FIG. 7). The appearance of anti-β2-GPI/oxLig-1 IgG antibody were correlated more highly with history of arterial thrombosis than with history of venous thrombosis or pregnancy morbidity (Table 3). On the other hand, significant correlation of these antibodies with thrombocytopenia was not observed. These findings suggest that β2-GPI/oxLig-1 (β2-GPI/oxLDL) complex is a true target antigen of aCL. The anti-β2-GPI/oxLig-1 IgG antibody is a powerful candidate for a factor inducing atherothrombosis/atherosclerosis based on autoimmune disease.

All of the examined patients with APS/SLE were divided into 2 groups, that is, β2-GPI/oxLDL complex positive and negative groups, and stronger relationship between the anti-β2-GPI/oxLig-1 antibody and the development of these clinical morbid states was observed in the positive group than in the negative group. In the autoantibody-positive patients with APS, IgG immune complexes containing β2-GPI and LDL were also observed. The mechanism of in vivo oxidation of LDL is unrevealed, but its oxidation product β2-GPI/oxLDL complex is considered to play a pathogenic role as autoimmune antigen inducing the occurrence of thrombosis, particularly arterial thrombosis, in APS.

George et al. have reported that LDL receptor-deficient mice given usual feed and immunized with β2-GPI have accelerated atherosclerosis [reference 17]. β2-GPI is present abundantly under endothelium and in an intimal-medial border of human atherosclerotic plaque, and occurs together with monocytes and CD4-positive lymphocytes [reference 18]. Accordingly, the circumstantial evidence of the autoimmune mechanism in which β2-GPI and oxLDL in generation of atheroma of APS are involved is further increased.

This is the first report that a stable and indissociable β2-GPI/oxLDL complex is found in patient serum, and this complex would be a quantifiable risk factor with respect to arterial thrombosis in APS. However, the β2-GPI/oxLDL complex is observed not only in APS but also in antibody-negative and non-thrombus SLE and in chronic nephritis. This indicates that given only the level of the complex in serum, the clinical condition of APS cannot be predicted. Abnormalities in lipid and lipoprotein metabolism are common among various renal diseases and hyperlipemia, and are understood to increase plasma lipoproteins such as LDL involved in high mortality and high occurrence of atherosclerotic cardiovascular disorder in patients with renal diseases. These findings raise an important and new problem for clinical significance of the β2-GPI/oxLDL complex circulating in blood in patients with coronary artery diseases.

Preparation of the Kit of the Present Invention (1) The kit 1 of the present invention constituted as shown below was prepared.
1. β2-GPI/oxLDL complex (1 mg) (standard) obtained by incubating oxLDL12h at pH 7.4, 37° C. for 16 hours together with β2-GPI
2. One 96-well immune plate
   Anti-β2-GPI antibody (WB-CAL-1), one tube 3. Biotin-labeled anti-apoB100 antibody (1D2)
4. HRP-labeled avidin
5. o-Phenylene diamine solution, 1 tube
6. Aqueous hydrogen peroxide, 1 tube
7. Reaction termination solution (1 N HCl), 1 tube (2) The kit 2 of the present invention constituted as shown below was prepared.
1. One 96-well immune plate on which the β2-GPI/oxLDL complex obtained by incubating oxLDL12h at pH 7.4, 37° C. for 16 hours together with β2-GPI was immobilized
2. HRP-labeled anti-human IgG antibody
3. o-Phenylene diamine solution, 1 tube
4. Aqueous hydrogen peroxide, 1 tube

REFERENCES

1. J. Exp. Med., 179, pp. 457-462 (1994)
2. Blood, 87, pp. 3262-3270 (1996)
3. EMBO J., 18, pp. 5166-5174 (1999)
4. J. Mol. Biol., 304, pp. 927-939 (2000)
5. Biochemistry, 40, pp. 8092-8100 (2000)
6. Clin. Exp. Immunol., 107, pp. 569-573 (1997)
7. J. Lipid Res., 42, pp. 697-709 (2001)
8. J. Immunol., 149, pp. 1063-1068 (1992)
9. Arthritis Rheum., 37, pp. 1453-1461 (1994)
10. J. Immunol., 148, pp. 3885-3891 (1992)
11. J. Clin. Invest., 43, pp. 1345-1353 (1955)
12. Anal. Biochem., 95, pp. 351-358 (1979)
13. Int. Immunol., 12, pp. 1183-1192 (2000)
14. Anal. Biochem., 213, pp. 79-89 (1993)
15. J. Lipid Res., 36, pp. 1876-1886 (1995)
16. J. Lipid Res., 38, pp. 1347-1360 (1997)
17. Circulation, 98, pp. 1108-1115 (1998)
18. Circulation, 99, pp. 2227-2230 (1999)

INDUSTRIAL APPLICABILITY

When the standard of the present invention is used, the β2-GPI/oxLDL complex occurring particularly in the living body can be measured more accurately and strictly, by which the measurement method 1 of the present invention, the detection method 1 of the present invention and the kit 1 of the present invention can be provided, and thus the standard of the present invention is extremely useful.

When the antigen of the present invention is used, "antibody recognizing β2-GPI/oxLDL complex" occurring particularly in the living body can be measured more accurately and strictly, by which the measurement method 2 of the present invention, the detection method 2 of the present invention, the solid phase of the present invention and the kit 2 of the present invention can be provided, and thus the antigen of the present invention is extremely useful. The measurement method 3 of the present invention can easily and rapidly detect an IgG immune complex formed with β2-GPI or LDL and is thus extremely useful.

The invention claimed is:

1. A standard for measuring oxidized LDL/β2-GPI complex in a sample, which comprises a complex having oxidized LDL bound covalently to β2-GPI, wherein the complex has the following properties (a) and (b):
    (a) oxidized LDL and β2-GPI constituting the complex are substantially not dissociated in the presence of 100 U/ml heparin, and
    (b) oxidized LDL and β2-GPI constituting the complex are substantially not dissociated in the presence of 10 mM $MgCl_2$.

2. A standard for measuring oxidized LDL/β2-GPI complex in a sample, which comprises a covalently bound oxidized LDL/β2-GPI complex obtainable by incubating oxidized LDL and β2-GPI under the conditions of 37° C. and pH 7.4 for 16 hours, wherein the complex has the following properties (a) and (b):
    (a) oxidized LDL and β2-GPI constituting the complex are substantially not dissociated in the presence of 100 U/ml heparin, and
    (b) oxidized LDL and β2-GPI constituting the complex are substantially not dissociated in the presence of 10 mM $MgCl_2$.

3. The standard according to claim 1, wherein the sample is a sample derived from a living body.

4. The standard according to claim 3, wherein the sample derived from a living body is blood.

5. A kit for measuring a covalently bound oxidized LDL/β2-GPI complex in a sample, which comprises the standard according to claim 1.

6. The measurement kit according to claim 5, further comprising an antibody capable of recognizing the covalently bound oxidized LDL/β2-GPI complex.

7. The measurement kit according to claim 5, which is used in detection of a disease.

8. An antigen for measuring an antibody capable of recognizing oxidized LDL/β2-GPI complex in a sample, which comprises a complex having oxidized LDL bound covalently to β2-GPI.

9. An antigen for measuring an antibody capable of recognizing oxidized LDL/β2-GPI complex in a sample, which comprises a covalently bound oxidized LDL/β2-GPI complex obtainable by incubating oxidized LDL and β2-GPI under the conditions of 37° C. and pH 7.4 for 16 hours.

10. The antigen according to claim 9, wherein the covalently bound oxidized LDL/β2-GPI complex obtainable by incubating oxidized LDL and β2-GPI under the conditions of 37° C. and pH 7.4 for 16 hours has the following properties (a) and (b):
    (a) oxidized LDL and β2-GPI constituting the complex are substantially not dissociated in the presence of 100 U/ml heparin, and
    (b) oxidized LDL and β2-GPI constituting the complex are substantially not dissociated in the presence of 10 mM $MgCl_2$.

11. A solid phase having the antigen according to claim 8 immobilized thereon.

12. A kit for measuring an antibody capable of recognizing the covalently bound oxidized LDL/β2-GPI complex in a sample, which comprises the solid phase according to claim 11.

13. The measurement kit according to claim 12, which further comprises a substance capable of binding to the antibody capable of recognizing a covalently bound oxidized LDL/β2-GPI complex.

14. The measurement kit according to claim 13, which is used in detection of a disease.

* * * * *